(12) United States Patent
Chatterjee

(10) Patent No.: US 6,782,891 B2
(45) Date of Patent: Aug. 31, 2004

(54) PROCESS FOR THE ISOLATION OF A MAJOR HARMFUL OXIDANT FROM CIGARETTE SMOKE

(75) Inventor: Indu Bhusan Chatterjee, Calcutta (IN)

(73) Assignee: Council of Scientific and Industrial Research, New Delhi (IN)

( * ) Notice: Subject to any disclaimer, the term of this patent is extended or adjusted under 35 U.S.C. 154(b) by 199 days.

(21) Appl. No.: 10/076,033

(22) Filed: Feb. 13, 2002

(65) Prior Publication Data

US 2003/0111087 A1 Jun. 19, 2003

(30) Foreign Application Priority Data

Jun. 22, 2001 (IN) ...................................... 701/DEL/2001

(51) Int. Cl.$^7$ .......................... G01N 33/497; A24F 1/10
(52) U.S. Cl. ..................... 131/330; 73/23.33; 73/23.31; 73/23.2; 73/28.01
(58) Field of Search .......................... 131/330; 73/23.31, 73/23.33, 23.32, 23.2, 28.01

(56) References Cited

U.S. PATENT DOCUMENTS 4,140,003 A * 2/1979 Pillsbury, Jr. et al. ..... 73/23.31
5,854,000 A * 12/1998 Bucala et al. ................ 435/7.1

\* cited by examiner

Primary Examiner—Dionne A. Walls
(74) Attorney, Agent, or Firm—Ohlandt, Greeley, Ruggiero & Perle, L.L.P.

(57) ABSTRACT

The components of cigarette smoke, known until now, do not explain the overwhelming hazardous effects of smoking; this invention describes the isolation, identification and procedures for determination of the structure, properties and assay of a relatively stable major harmful oxidant (cs-oxidant) present in the cigarette smoke, the content of which is about 190±10 μg per cigarette; the cs-oxidant alone almost quantitatively accounts for the oxidative damage of proteins produced by the aqueous extract of whole cigarette smoke, it is also responsible for the oxidative damage of DNA; since the cs-oxidant is relatively stable, it further explains the deleterious effects of the side stream smoke and passive smoking; a number of chemical compounds/agents including vitamin C have been found to prevent the cs-oxidant induced protein oxidation in vitro.

18 Claims, 35 Drawing Sheets

Figure 1:
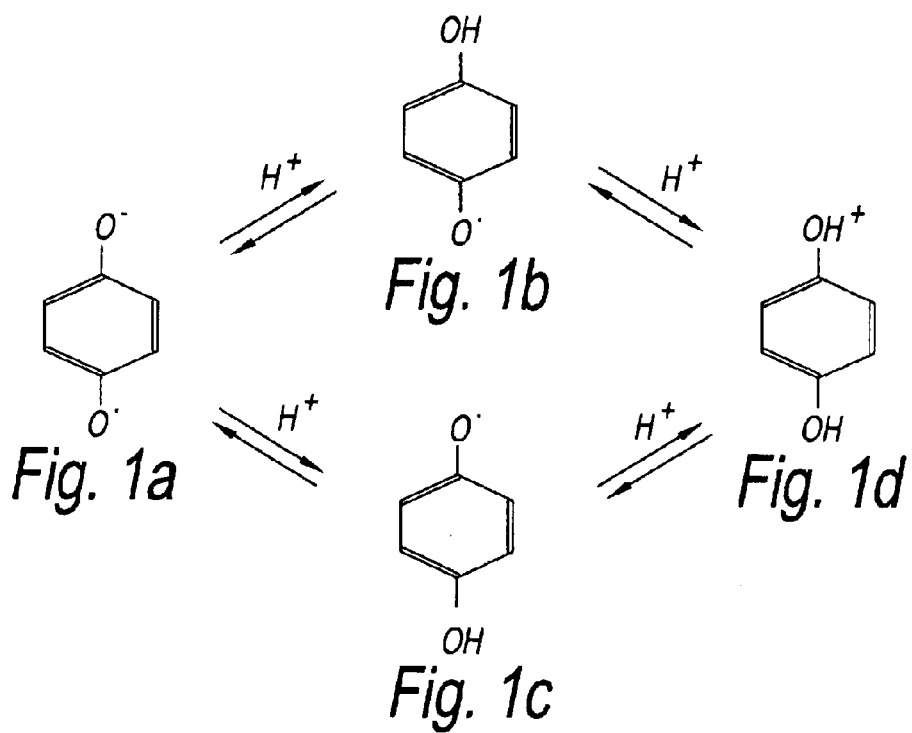

Mesomeric forms of p-benzosemiquinone. (a) anionic; (b),(c) neutral; (d) cationic.

Band thin layer chromatography of the methanol solution after lyophilization (step 5) ⟶ Indicates the band of the cs-oxidant.

*HPLC profile the butanol extract after TLC. The cs-oxidant (step 6) eluted as a major peak at the retention time of 8.808 min. The amount of cs-oxidant eluted was ≈ 12 μg.*

| CHROMATOPAC | C-R6A | | | | | |
|---|---|---|---|---|---|---|
| SAMPLE NO | 0 | | FILE | 0 | | |
| REPORT NO | 35 | | METHOD | 41 | | |

| PKNO | TIME | AREA | MK | IDNO | CONC | NAME |
|---|---|---|---|---|---|---|
| 1 | 8.808 | 387815 | | | 100 | |
| | TOTAL | 387815 | | | 100 | |

HPLC profile of the pure cs-oxidant, eluted at the retention time of 8.808 min.

Thin layer chromatography of the pure cs-oxidant ($R_f = 0.26$)

Fluorescence spectroscopic profile of the cs-oxidant in methanol. The excitation was at 293 nm and the emission scanning was measured from 300 nm to 800 nm. The emission maxima were at 329.6 nm and at 651.4 nm.

| CX WAVELENGTH | 224 nm |
| --- | --- |
| CX BANDPASS | 5 nm |
| CM BANDPASS | 5 nm |

SCAN SPEED: 240 nm/min
RESPONSE  2 sec

| NO. | PEAK | | VALLEY | |
| --- | --- | --- | --- | --- |
| 1 | 329.6 nm | 502.2 | 261.2 nm | 0.524 |
| 2 | 454.6 nm | 41.39 | 228.6 nm | 3.647 |
| 3 | 405.4 nm | 3.563 | 476.4 nm | 2.356 |
| 4 | 652.6 nm | 121.2 | 527.6 nm | 1.114 |

Fluorescence spectroscopic profile of the cs-oxidant in methanol. The excitation was at 224 nm and the emission scanning was measured from 225 nm to 800 nm. The emission maxima were at 329.6 nm and at 652.6 nm.

| | | | EM WAVELENGTH | 330 nm |
|---|---|---|---|---|
| EX BANDPASS | 5 nm | | SCAN SPEED: | 240 nm/min |
| EM BANDPASS | 5 nm | | RESPONSE | 2 sec |

| NO. | PEAK | | VALLEY | |
|---|---|---|---|---|
| 1 | 228.2 nm | 1115 | 252.4 nm | 77.46 |
| 2 | 293.8 nm | 1174 | | |

Fluorescence spectroscopic profile of the cs-oxidant in methanol. The emission was at 330 nm and the excitation scanning was measured from 220 nm to 325 nm. The excitation maxima were at 228.2 nm and at 293.8 nm.

| CX BANDPASS | 5 nm | EM WAVELENGTH 651 nm |
| CM BANDPASS | 5 nm | SCAN SPEED: 240 nm/min |
|  |  | RESPONSE 2 sec |

| NO. | PEAK |  | VALLEY |  |
|---|---|---|---|---|
| 1 | 229.2 nm | 267.2 | 252.2 nm | 19.04 |
| 2 | 294.8 nm | 200.0 | 320.0 nm | 7.691 |
| 3 | 325.0 nm | 31.90 | 370.2 nm | 0.095 |
| 4 | 597.0 nm | 21.70 | 642.0 nm | 0.513 |

Fluorescence spectroscopic profile of the cs-oxidant in methanol. The emission was at 651 nm and the excitation scanning was measured from 220 nm to 650 nm. The excitation maxima were at 229.2 nm and at 294.8 nm.

Crystal structure of the pure cs-oxidant

UV spectrophotometric profile of the cs-oxidant in methanol. It has two absorption maxima, one at 293.4 nm and another at 223.0 nm.

Stability of the solid oxidant kept at 25°C under darkness. The stability was determined by its capacity to oxidize ascorbic acid. Ascorbic acid was mesured by HPLC analysis at 254 nm.

Standard curve of ascorbic acid based on HPLC analysis at 254 nm.

Stability of the cs-oxidant in 50 mM potassium phosphate buffer at 25°C measured by its potency to oxidize ascorbate as evidenced by HPLC area.

Quantitative reduction of ferricytochrome c by the oxidant as measured by the formation of ferrocytochrome c with time at 550 nm. The reaction was carried out in 50 mM potassium phosphate buffer, pH 7.4, keeping the final concentration of ferricytochrome c at 100 $\mu$M. One nmole of the oxidant reduced 0.71 nmoles of ferricytochrome c.

Standard curve of the oxidant on the basis of HPLC area at 294 nm. Different amounts of the cs-oxidant were used ranging from 10 ng to 100 ng in 20 μl of mobile solvent.

Standard curve of the oxidant on the basis of reduction of cytochrome c by using different amounts of the oxidant ranging from 1 μg to 5 μg.

Mass spectrum of the pure cs-oxidant.

| SCAN SPEED: 120.0 nm/min | | | RESPONSE: MEDIUM | |
|---|---|---|---|---|
| BANDPASS: 2.00nm | | | | |
| NO. | PEAK | | VALLEY | |
| 1 | 293.8 nm | 0.2443 Abs | 253.0 nm | 0.0137 Abs |
| 2 | 224.2 nm | 0.4837 Abs | 214.4 nm | 0.3979 Abs |

UV spectrophotometric profile of the hydroquinone in methanol. It has two absorption maxima, one at 293.8 nm and another at 224.2 nm.

SCAN SPEED: 120.0 nm/min  RESPONSE: MEDIUM
BANDPASS: 2.00nm

| NO. | PEAK | | VALLEY | |
|---|---|---|---|---|
| 1 | 293.6 nm | 0.2772 Abs | 252.8 nm | 0.0269 Abs |
| 2 | 224.4 nm | 0.5476 Abs | 214.0 nm | 0.4314 Abs |

UV spectrophotometric profile of the cs-oxidant stored at room temperature in dark for 8 days. The two absorption maxima are at 293.6 nm and at 224.4 nm.

SCAN SPEED: 120.0 nm/min  RESPONSE: MEDIUM
BANDPASS: 2.00nm

| NO. | PEAK | | VALLEY | |
|---|---|---|---|---|
| 1 | 293.8 nm | 0.5855 Abs | 263.4 nm | 0.1407 Abs |
| 2 | 225.2 nm | 1.2232 Abs | 209.6 nm | 0.8263 Abs |

UV spectrophotometric profile of equimolar mixture of p-benzoquinone and hydroquinone in methanol. There is a shoulder near 242 nm (the $\lambda_{max}$ of p-benzoquinone).

Fluorescence spectroscopic profile of the hydroquinone in methanol. The excitation was at 294 nm and the emission scanning was measured from 300 nm to 800 nm. The emission maxima were at 329.4 nm and at 651.6 nm.

FTIR spectroscopic profile of the cs-oxidant.

FTIR spectroscopic profile of hydroquinone.

H-NMR spectroscopic profile of the cs-oxidant in $CD_3COCD_3$.

H-NMR spectroscopic profile of hydroquinone in $CD_3COCD_3$.

Comparative H-NMR spectroscopic profiles of (a) cs-oxidant and (b) hydroquinone.

H-NMR spectroscopic profile of the cs-oxidant after reduction with sodium dithionite.

C-NMR spectroscopic profile of hydroquinone in $CD_3COCD_3$.

Room temperature ESR spectrum of cs-oxidant, freshly prepared from 100 cigarettes. The spectrum was recorded on a JES-REIX ESR spectrometer (Tokyo, Japan). The spectral parameters were as follows: microwave frequency, 9.435 GHz; power, 2mW; field modulation width, 0.4mT; modulated frequency, 100 kHz; time constant, 0.3 sec; scan rate, 2.5 mT/sec.

Room temperature ESR spectrum of aged (10 days) cs-oxidant, prepared from 400 cigarettes.

| CHROMATOPAC | C-R6A | | | | | |
|---|---|---|---|---|---|---|
| SAMPLE NO | 0 | | | FILE | 0 | |
| REPORT NO | 48 | | | METHOD | 41 | |
| PKNO | TIME | AREA | MK | IDNO | CONC | NAME |
| 1 | 5.717 | 475376 | | | 19.0777 | |
| 2 | 6.157 | 317530 | V | | 12.7431 | |
| 3 | 6.58 | 209664 | V | | 8.4142 | |
| 4 | 7.175 | 708579 | V | | 28.4366 | |
| 5 | 8.813 | 340583 | V | | 13.6682 * | |
| 6 | 9.83 | 99028 | V | | 3.9742 | |
| 7 | 10.37 | 103590 | V | | 4.1573 | |
| 8 | 11.28 | 178509 | V | | 7.1639 | |
| 9 | 13.367 | 24236 | V | | 0.9727 | |
| 10 | 14.117 | 15200 | V | | 0.61 | |
| 11 | 16.75 | 9187 | | | 0.3687 | |
| 12 | 17.782 | 10303 | | | 0.4135 | |
| | TOTAL | 2491784 | | | 100 | |

HPLC profile of the whole cs solution analyzed in the silica column (LiChrospher® Si 60, Merck).
* indicates the retention time, area and the concentration (13.6682%) of the cs-oxidant.

| PKNO | TIME | AREA | MK | IDNO | CONC | NAME |
|---|---|---|---|---|---|---|
| 1 | 5.092 | 6469 | | | 0.5956 | |
| 2 | 6.183 | 43150 | V | | 3.9726 | |
| 3 | 6.557 | 54830 | V | | 5.048 | |
| 4 | 7.17 | 190600 | V | | 17.5478 | |
| 5 | 8.083 | 59275 | V | | 5.4572 | |
| 6 | 8.808 | 295731 | V | | 27.2269* | |
| 7 | 10.517 | 137178 | V | | 12.6295 | |
| 8 | 11.252 | 129369 | V | | 11.9105 | |
| 9 | 13.483 | 39852 | V | | 3.669 | |
| 10 | 14.125 | 37368 | V | | 3.4403 | |
| 11 | 15.257 | 16282 | V | | 1.499 | |
| 12 | 16.915 | 28634 | V | | 2.6362 | |
| 13 | 17.777 | 32483 | V | | 2.9906 | |
| 14 | 18.937 | 14954 | V | | 1.3768 | |
| | TOTAL | 1086173 | | | 100 | |

HPLC profile of the aqueous extract of cs solution analyzed in the silica column (LiChrospher® Si 60, Merck).
* indicates the retention time, area and the concentration (27.2269%) of the cs-oxidant.

HPLC profile of the whole cs solution analyzed in the ODS column (Shim-pack CLC -ODS, Shimadzu). The cs-oxidant eluted at 13.467 min.

HPLC profile of the pure cs-oxidant, analyzed in the CLC-ODS column (Shim-pack CLC-ODS, Shimadzu) eluted at the retention time of 13.458 min.

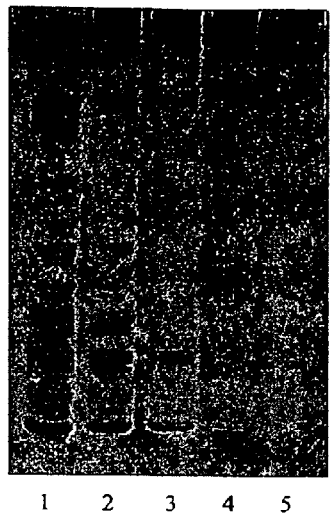

1  2  3  4  5

Fig. 35a

SDS-PAGE of the guinea pig lung microsomal proteins treated with whole cs solution and the cs-oxidant. Lane 1, untreated microsomes; lane 2, microsomes treated with 50 μl cs solution; lane 3, microsomes treated with 100 μl cs solution; lane 4, microsomes treated with 10 μg cs-oxidant; lane 5, microsomes treated with 20 μg cs-oxidant.

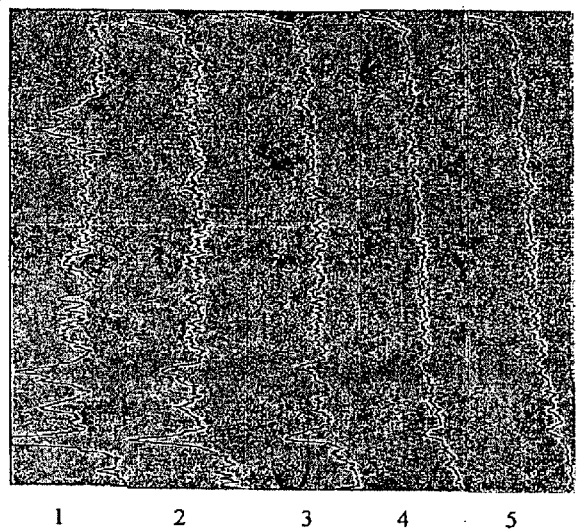

1  2  3  4  5

Fig. 35b

Densitometric scanning of the protein bands of different lanes as in Fig. 35a.

PROCESS FOR THE ISOLATION OF A MAJOR HARMFUL OXIDANT FROM CIGARETTE SMOKE

FIELD OF INVENTION

The present invention relates to a process for the isolation of p-benzosemiquinone of formula 1:

a major harmful oxidant from cigarette smoke. More particularly the present invention provides a process for the isolation of p-benzosemiquinone, a major harmful oxidant from cigarette smoke, which is responsible for the oxidative damage of proteins and DNA

BACKGROUND OF THE INVENTION

Exposure to cigarette smoke is a major cause of life-threatening diseases like bronchitis, emphysema, other diseases of the respiratory tract, coronary heart diseases, lung cancer and other malignancies [1–5]. In fact, cigarette smoke is the overwhelming cause of lung cancer, now the most common cancer globally. Since approaches to cessation of smoking by public health campaigns and anti-smoking laws passed by local Governments have had limited success, the most practicable approach is the prevention of the hazardous effects caused by cigarette smoke. Cigarette smoke in known to contain about 4000 components, out of which about 3000 components are present in the gas phase and about 1000 components in the tar phase [6]. The oxidants in the gas phase, such as $O_2^-$, $H_2O_2$, NO, peroxy radical are extremely unstable [7]. If the gas phase is passed into phosphate buffer and the resultant solution is added to albumin solution, no protein oxidation occurs (7). Apparently, any damage caused by the gas phase is expected to be restricted to the buccal cavity and upper respiratory tract [8]. On the other hand, the oxidant(s) present in the tar are quite stable and these are apparently responsible for producing oxidative damage in the lung, heart and other organs [7,9]. About 48 percent of the tar components are water soluble [10] and the aqueous extract of tar is known to produce oxidative damage of biological macromolecules including proteins and DNA [7,11,12]. However, it is perplexing to conceive how many of the components present in the aqueous extract of tar are responsible for producing oxidative damage in the biological system. Uptil now, among the many components of cigarette smoke, three classes of compounds have been suggested to be implicated as causative agents in the development of cancer and degenerative diseases, namely, (i) polycyclic aromatic hydrocarbons (ii) nitrosamines and (iii) free radicals.

Among the polycyclic hydrocarbons, benzo [a] pyrene is by far the best studied. But it is not a carcinogen and requires metabolic activation through cytochrome P450 system to become the ultimate carcinogen, benzo [a] pyrene diol epoxide. Moreover, the concentration of benzo [a] pyrene in cigarette smoke is meagre, about 10 to 40 ng per cigarette [13] and benzo [a] pyrene cannot explain oxidative damage of protein produced by cigarette smoke.

Among the tobacco specific nitrosamines (TSNA), the most studied ones are $N^1$-nitrosonornicotine (NNN) and 4-(methylnitrasamino)-1-(3-pyridyl)-1-butanone (NNK). Again TSNA are not direct carcinogens and also their concentrations in tobacco smoke vary widely. The observed range for NNN is 0.004 μg to 1.35 μg and for NNK, <0.004 μg to 1.75 μg per cigarette. It is concluded that TSNA in cigarette smoke is not a sufficient index for the carcinogenic potential of cigarette smoke [14]. Again TSNA cannot explain oxidative damage of proteins.

Another aspect of the hazardous component of cigarette smoke is free radical. Pryor and his associates made considerable studies on free radical chemistry of cigarette smoke and its toxicological implications. These authors suggest that the principal relatively stable free radical in cigarette tar may be a quinone/hydroquinone complex which is an active redox system and that this redox system is capable of reducing molecular oxygen to produce superoxide, leading to hydrogen peroxide and hydroxyl radicals [15], that may eventually lead to oxidative damage of biological macromolecules but we have observed that oxidative damage of proteins produced by the stable tar radicals is not inhibited by SOD or catalyst indicating that the oxidative damage is not mediated by super oxide radical or hydrogen peroxide. The applicants have further observed that the tar radicals oxidize proteins in nitrogen atmosphere and in the absence of molecular oxygen, indicating a direct interaction of the tar radicals with biological micromolecules. However, these authors admit that the principal radical they have identified in tar is actually not a monoradical and probably is not a single species (16). They also admit that cigarette tar is an incredibly complex mixture and since the tar radicals have not been isolated and unambiguously identified, any conclusion concerning the chemistry or biochemistry of the tar radicals must be regarded as tentative [15].

It is noteworthy to mention that by the 1960s, the tobacco industry in general had proven in its own laboratory that cigarette tar causes cancer in animals [17]. Throughout 1960s the companies' researchers tried to discover the toxic elements in cigarette smoke with the conviction that if the toxic components could be identified, these agents could be removed or eliminated and a "safe" cigarette could be created, which would deliver nicotine without delivering the toxic substances [17]. But by the late 1970s, the tobacco industry had largely abandoned this particular research, because the objective proved to be unattainable. It was a problem technically difficult to solve and proved untractable [17].

Very recently, we have observed that aqueous extract of whole cigarette smoke/tar contains a major harmful oxidant in relatively high amount, approximately 190±10 μg per cigarette. The applicants have isolated the oxidant, determined the structure and found it to be p-benzosemiquinone. The oxidant almost quantitatively accounts for the oxidative damage of proteins produced by the aqueous extract of whole cigarette smoke/tar. The oxidant is also responsible for DNA oxidation. Nagata et al. (18) have shown that semiquinone radicals bind to DNA and damage it. It is also known that oxidative damage of DNA is implicated with mutation and cancer. The oxidant is relatively stable. Its half-life in the solid state at room temperature is approximately 48 hours. The presence of the stable oxidant in cigarette smoke would explain the deleterious effects of side stream smoke and passive smoking (7). The oxidant is absent in nonsmoking tobacco and is produced during burning of the cigarette (7). Applicants have identified a number of chemical compounds/agents those deactivate the oxidant and may be used as antidotes.

OBJECTS OF THE INVENTION

Main object of the present invention relates to isolation and characterization of a major harmful oxidant from aqueous extract of whole cigarette smoke/tar, which is mainly responsible for the oxidative damage of biological macromolecules including proteins and DNA.

Another object of the invention is to provide a method for the quantitative assay of cigarette smoke (cs) oxidant present in the whole cigarette solution Still another object of the invention is to the identification of chemical compounds/agents those will deactivate the oxidant and act as antidotes for combating the harmful effect of the oxidant.

SUMMARY OF THE INVENTION

A relatively stable major harmful oxidant has been isolated from aqueous extract of whole cigarette smoke/tar and purified to the extent of >99% by differential solvent extraction, thin layer chromatography and preparative HPLC. The yield is about 16 μg per cigarette, which is about 8.4% of the amount (≈190 μg) present in the smoke of one cigarette. Comparable results were obtained from twelve different brands of commercial cigarettes. The purified oxidant crystallizes in fine needle shaped very pale yellow crystals from a solution in acetone. The structure of the oxidant has been found to be p-benzosemiquinone as evidenced by elemental analysis, mass spectrum, UV, fluorescence, IR, H-NMR, C-NMR and ESR spectroscopy as well as by chemical properties. The oxidant can be measured quantitatively by either UV absorption spectroscopy or HPLC.

In p-benzosemiquinone, the unpaired electron is delocalised over an aromatic framework containing heteroatoms leading to different mesomeric forms, namely, anionic, neutral and cationic forms (FIG. 1, see ref. 19). This resonance would explain the stability of the semiquinone. The half-life of the oxidant stored in the solid state at the room temperature in air and under darkness is about 48 hours as determined by its capacity to oxidize ascorbic acid. In aqueous solution at pH 7.4, the half-life is about 1.5 hours. Using oxidation of BSA or oxidative degradation of guinea pig lung microsomal proteins as model systems, the oxidant quantitatively accounts for the oxidative damage produced by the aqueous extract of whole cigarette smoke. The cs-oxidant is also responsible for DNA oxidation.

A number of chemical compounds/agents have been identified those inactivate the oxidant and act as antidotes.

DETAILED DESCRIPTION OF THE INVENTION

Accordingly, the present invention provides a process for the isolation of p-benzosemiquinone of formula 1, a harmful oxidant and the compound identified to counteract the harmful effect caused by this oxidant.

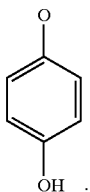

In an embodiment of the present invention, provides a process for isolating the major harmful oxidant from cigarette smoke responsible for the oxidative damage of proteins and DNA, the said process comprising the steps of:

a) obtaining tar solution from lighted conventional filter tipped cigarette in a glass flask dipped in a mixture of ice and salt;

b) allowing the tar to condense and settle at the bottom of the flask to obtain whole cs solution;

c) extracting the said tar with 30–60 mM potassium phosphate buffer at a pH ranging between 7.4 to 7.8;

d) filtering the solution of step (c) through 0.45 μm Millipore filter;

e) adjusting the pH of the filtrate obtained from step (d) by aqueous NaOH solution to obtain the desired cigarette smoke aqueous extract solution, f) extracting the above said cs aqueous solution thrice using equal volume of methylene chloride, discarding the lower methylene chloride layer and collecting the upper yellow colored semi purified extract of cigarette smoke solution;

g) further extracting the aqueous extract of cigarette smoke of step (f) twice using equal volume of water-saturated n-butanol, pooling yellow n-butanol extract and lyophilizing at a temperature ranging between −50° C. to −60° C. under vacuum;

h) extracting the lyophilized material of step (g) twice using HPLC grade acetone to obtain acetone soluble extract;

i) drying the acetone soluble extract of step (h) under vacuum to yield a residue;

j) dissolving the residue of step (i) in HPLC grade methanol;

k) subjecting methanol solution of steps) to preparative TLC using non-fluorescent silica plates, developing the said silica plates using a solvent system constituting mixture of toluene and ethyl acetate in a ratio of 80:20, taking out the plate, drying at about 25–30° C. using a drier, cutting small strips containing the developed material from both sides of the plates and keeping them in an iodine chamber for the location of the band corresponding to Rf 0.26, scraping the band and extracting the band material with HPLC grade acetone, filtering and collecting the acetone solution and drying under vacuum to get a pale yellow residue; and l) dissolving the residue of step (k) by adding equal volume of milli Q water, extracting the aqueous solution with equal volume of HPLC grade water saturated n-butanol and finally followed by drying upper n-butanol layer in small glass tubes under vacuum to obtain the major cigarette smoke (cs) oxidant with a purity of 98–99% and yield of 18–22 μg per cigarette, In an embodiment of the present invention, wherein said cs oxidant obtained from step (l) is further purified by HPLC after dissolving in a mobile phase comprising a mixture of methylene chloride and methanol in a ratio of 90:10 (v/v) and injecting it in a HPLC instrument with a normal phase 25 cm silica column using a UV detector at 294 nm at a flow rate of 0.5 ml/min, at a temperature of about 25° C., at a pressure of about 29 kgf/cm$^2$, collecting the effluent which appears as a single peak at a retention time of 8.808 min with a purity of 100% and yield of about 8.4% of the total cs oxidant (p-benzosemiquinone) present in the parent cs solution.

In another embodiment of the invention, wherein primary cs solution of step (a) is also obtained from lighted convention filter cigarette by passing the whole cigarette smoke into 30–60 mM potassium buffer at pH 7.4–7.8, filtering the above solution through 0.45 μm Millipore filter, adjusting the pH to 7.4 to 7.6 of the filtrate by adding aqueous NaOH solution and performing steps (b) to (l) for obtaining the major cs oxidant p-benzosemiquinone.

Another embodiment of the invention, wherein the said isolated pure cigarette smoke (cs) oxidant p-benzosemiquinone has the following characteristics:

a) on crystallizing with acetone to form small faint yellow needle crystals, having pungent smell similar to that of rancid butterfat, b) UV absorption maxima in methanol solution are at 293.4 nm and 223.0 nm and in aqueous solution are in 288 nm and 221 nm respectively, c) on excitation at 293 nm in methanol solution the observed emission maxima are at 329.6 nm and 651.4 nm and on excitation at 224 nm, the observed emission maxima are at 329.6 nm and 652.6 nm respectively, d) monitoring on excitation scanning keeping the emission wavelength at 330 nm, the observed excitation maxima are at 228.2 nm and 293.8 nm and when the emission is kept at 651 nm and excitation scanning is monitored, the observed excitation maxima are at 229.2 nm and 294.8 nm respectively, e) highly soluble in methanol, ethanol, acetone, n-butanol, fairly soluble in water, sparingly soluble in methylene chloride, di-ethyl ether, chloroform and insoluble in benzene and petroleum ether, f) compound looses its oxidizing potency in acidic pH ranging between 4 to 5 and on keeping the solution at alkaline pH ranging between 9 to 10, the compound gradually turns brown, at pH 10 and above there is instantaneous darkening with loss of both activity and aromaticity as evidenced by UV spectroscopy, g) the half-life of the oxidant, when stored in the solid state at a temperature ranging between 25° C. to 30° C. under darkness is about 48 hours as determined by its oxidative potency, but in solution of 50 mM potassium phosphate buffer of pH 7.4 at 25° C. to 30° C. the half life is about 90 minutes, h) reduces ferricytochrome c and ferric chloride, i) oxidizes ascorbic acid, proteins and DNA, and j) the melting point is 162° C., Still another embodiment of the invention, wherein p-benzosemiquinone present in cs solution is quantitatively assayed by HPLC with a UV detector using a 25 cm reverse phase ODS column and using a mixture of water and methanol (95:5 v/v) as a mobile phase, at a wave length of 288 nm, flow rate of 0.8 ml/min, at a temperature of about 25° C. and at a pressure of about 147 Kgf/cm$^2$ and having a retention time of 13.46 min.

Yet another embodiment of the invention, wherein the said p-benzosemiquinone isolated from the whole cs solution is responsible for the major cause of oxidative damage of proteins.

Yet another embodiment of the invention, wherein p-benzosemiquinone, the cs oxidant is responsible for the oxidative damage of DNA.

Still yet another embodiment of the invention, wherein the damage of proteins caused by p-benzosemiquinone present in cs solution is quantitatively determined by measuring protein carbonyl formation by reacting the protein with p-benzosemiquinone obtained from the cs solution, followed by reaction with 2,4 dinitrophenyl hydrazine (DNPH) and finally measuring the absorbance at a wave length of 390 nm.

In yet another embodiment of the invention, wherein the damage of proteins caused by p-benzosemiquinone present in cs solution is quantitatively determined by measuring oxidative degradation of guinea pig tissue microsomal proteins by reacting the said protein with p-benzosemiquinone present in cs solution followed by SDS-PAGE and densitometric scanning.

Yet another embodiment of invention, wherein the protein used for the assay of oxidative damages of protein is selected from the group consisting of BSA and guinea pig lung microsomal proteins Yet another embodiment of the invention, wherein the BSA oxidation produced by the whole cs solution is effected by the p-benzosemiquinone present in the cs solution.

In yet another embodiment of the invention, the BSA oxidation produced by the cs oxidant as evidenced by nmoles of carbonyl formed per mg BSA is 9.56±0.14 in comparison to 7.53±0.34 produced by the whole cs solution.

In yet another embodiment of the invention, the BSA oxidation produced by the cs oxidant is evidenced by nmoles of carbonyl formed per mg BSA is 9.56±0.14 in comparison to 8.16±0.24 produces by the aqueous extract of cigarette smoke.

In yet another embodiment of the invention, the BSA oxidation produced by the cs oxidant is evidenced by nmoles of carbonyl formed per mg BSA is 9.56±0.14 in comparison to 9.23±0.14 produces by the TLC purified aqueous extract of cigarette smoke.

In yet another embodiment of the invention, the oxidative degradation of guinea pig tissue microsomal proteins produced by the p-benzosemiquinone solution is evidenced by SDS-PAGE is comparable to that produced by the whole cs solution.

In yet another embodiment of the invention, wherein the said method is used for quantitative determination of cs oxidant p-benzosemiquinone in cigarettes based on the tar content of the particular commercial brand of the cigarette.

In yet another embodiment of the invention, wherein the said method is used for quantitative determination of cs oxidant p-benzosemiquinone in cigarettes based on toxicity level of the particular commercial brand of the cigarette.

One more embodiment of the invention relates to a method for the prevention of cigarette smoke induced protein oxidation in vitro, said method comprises inhibiting the BSA oxidation by using a chemical compound or agent selected from the group consisting of ascorbic acid, sodium dithionite, tartaric acid, citric acid, oxalic acid, succinic acid, histidine, lysine, thiourea, glutathione, black tea extract, green tea extract, catechin, epigallocatechin and epicatechin.

In another embodiment of the invention, wherein ascorbic acid inhibits BSA oxidation up to 76% at a concentration of about 100 μM.

In still another embodiment of the invention, wherein Sodium dithionite inhibits BSA oxidation up to 97% at a concentration of about 2 mM.

Still another embodiment of the invention, wherein tartaric acid inhibits BSA oxidation up to 75% at a concentration ranging between 500 μM and 1 mM.

In yet another embodiment of the invention, wherein citric acid inhibits BSA oxidation up to 75% at a concentration ranging between 500 μM and 1 mM.

In yet another embodiment of the invention, wherein oxalic acid inhibits BSA oxidation up to 53% at a concentration of about 500 μM.

In yet another embodiment of the invention, wherein succinic acid inhibits BSA oxidation up to 60% at a concentration of about 1 mM.

In yet another embodiment of the invention, wherein histidine acid inhibits BSA oxidation up to 67% at a concentration of about 1 mM.

In another embodiment of the invention, wherein black tea extract inhibits BSA oxidation up to 50% at a concentration of about 2.5 mg.

Yet another embodiment of the invention, wherein catechin inhibits BSA oxidation up to 54% at a concentration range of about 750 μg.

Yet another embodiment of the invention, wherein epigallocatechin inhibits BSA oxidation up to 95% at a concentration of about 140 μg.

Yet another embodiment of the invention, wherein epicatechin inhibits BSA oxidation up to 50% at a concentration of about 50 μg.

Yet another embodiment of the invention, wherein green tea extract inhibits BSA oxidation up to 50% at a concentration of about 2.5 mg.

Yet another embodiment of the invention, wherein lysine inhibits BSA oxidation up to 35% at a concentration of about 1 mM.

Yet another embodiment of the invention, wherein thiourea inhibits BSA oxidation up to 52% at a concentration of about 10 mM.

Yet another embodiment of the invention, wherein glutanthione inhibits BSA oxidation up to 37% at a concentration of about 1 mM.

One more embodiment of the invention relates antidotes for the harmful effect caused by the cigarette smoke oxidant which are selected from the group consisting of ascorbic acid, sodium dithionite, tartaric acid, citric acid, oxalic acid, succinic acid, histidine, lysine, thiourea, glutathione, black tea extract, green tea extract, catechine, epigallocatechin and epicatechin.

Still another embodiment of the invention relates to use of the compound p-benzosemiquinone for studying the mechanism of oxidative damage-induced degenerative diseases and cancer caused by cigarette smoke producing oxidative damage to isolated protein, DNA, cultured cells or to an experimental model under laboratory conditions.

One more embodiment of the present invention relates to a method for quantitative estimation of an harmful oxidant, p-benzosemiquinone, the said method is helpful in formulating the quantity and nature of smoking material to be used in cigarette, cigar, cigarette pipes and any other convention smoking devices.

In still another embodiment of the present invention provides a method for the prevention of cigarette smoke induced protein oxidation in vitro, the said method comprises inhibiting the BSA oxidation by using a chemical compound or agent selected from the group consisting of ascorbic acid, sodium dithionite, tartaric acid, citric acid, oxalic acid, succinic acid, histidine, lysine, thiouria, glutathione, black tea extract, green tea extract, catechine, epigallocatechin and epicatechin, the said inhibition of BSA oxidation is shown below in a tabular form.

Protection of cs-oxidant-induced albumin oxidation by different chemical agents

| Ser. No. | Agents used | Concentration/amount | % Protection |
|---|---|---|---|
| 1. | Ascorbic acid | 100 μM | 76 |
| 2. | Sodium dithionite | 2 mM | 97 |
| 3. | Tartaric acid | 1 mM | 75 |
|  | Tartaric acid | 500 μM | 67 |
| 4. | Citric acid | 1 mM | 75 |
|  | Citric acid | 500 μM | 67 |
| 5. | Oxalic acid | 500 μM | 53 |
| 6. | Succinic acid | I mM | 60 |
| 7. | Histidine | 1 mM | 67 |
| 8. | Black tea extract | 2.5 mg | 50 |
| 9. | Catechin | 750 μg | 54 |
| 10. | Epigallocatechin | 140 μg | 95 |
| 11. | Epicatechin | 50 μg | 50 |
| 12. | Green tea extract | 2.5 mg | 50 |
| 13. | Lysine | 1 mM | 35 |
| 14. | Thiourea | 10 mM | 52 |
| 15. | Glutathione | 1 mM | 37 |

In still another embodiment the compound p-benzosemiquinone is useful in effecting oxidative damage to isolated protein, DNA or cultured cells under laboratory conditions to enable study of the mechanism of oxidative damage-induced degenerative diseases and cancer caused by cigarette smoke.

The present invention is described with reference to examples herein below, which are illustrative only and should not be construed to limit the scope of present invention in any manner.

BRIEF DESCRIPTION OF THE ACCOMPANYING DRAWINGS

Figure 2:
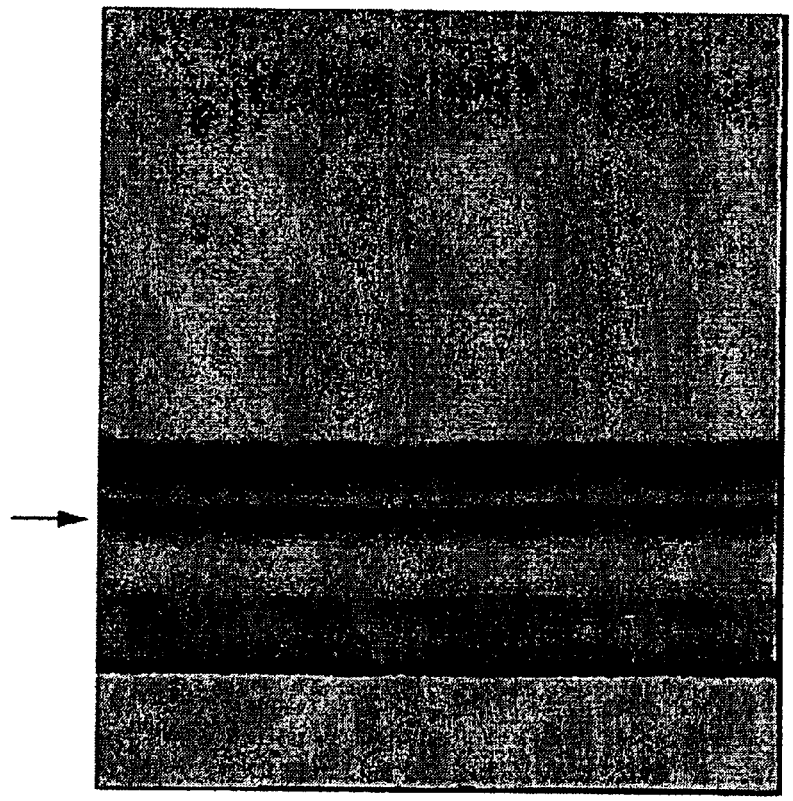
Figure 3:
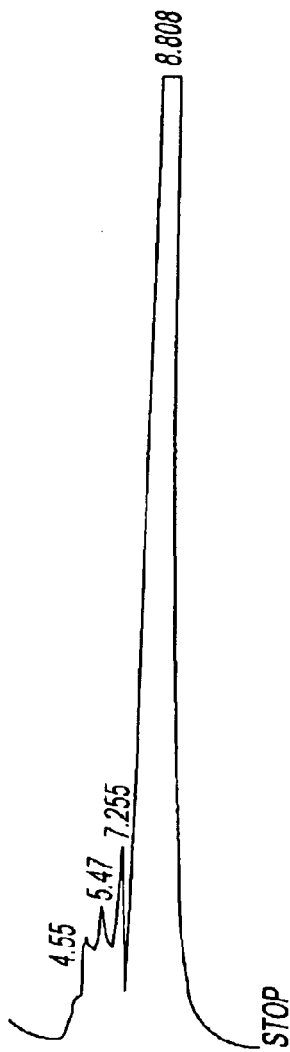

FIG. 1 shows Mesomeric forms of p-benzosemiquinone, a) anionic, b) and c) neutral and d) cationic;

FIG. 2 Band thin layer chromatography of the methanol solution after lyophilization—indicates the band of the cs-oxidant FIG. 3 HPLC profile of the butanol extract after TLC The cs-oxidant (step 6) eluted as a major peak at the retention time of 8.808 min. The amount of cs-oxidant eluted was ~12 μg.

Figure 4:
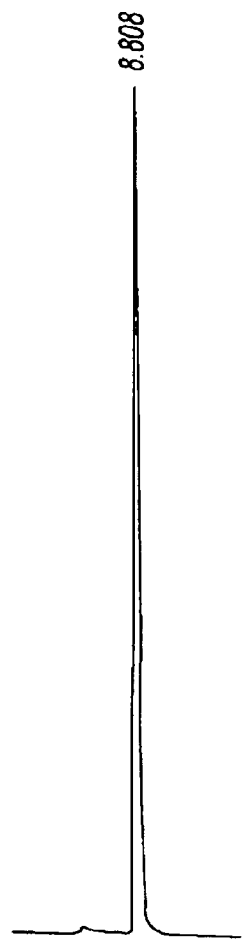

FIG. 4 HPLC profile of the pure cs-oxidant, eluted at the retention time of 8.808 mon.

Figure 5:

FIG. 5 Thin layer chromatography of the pure cs-oxidant ($R_f$=0.26)

Figure 6A:
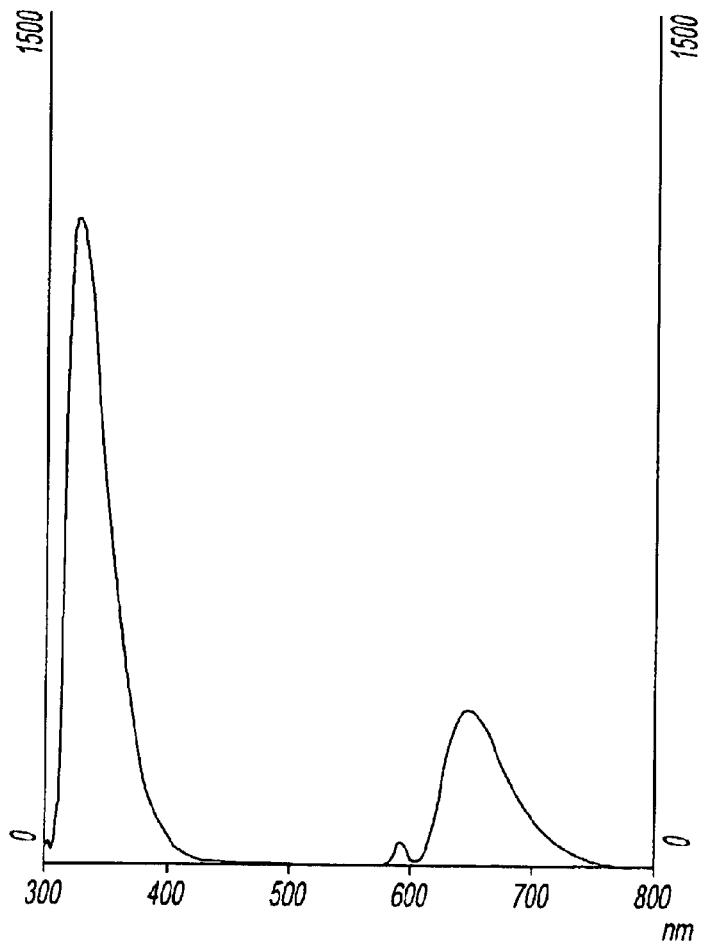

FIG. 6a Fluorescence spectroscopic profile of the cs-oxidant in methanol. The excitation was at 293 nm and emission scanning was measured from 300 nm to 800 nm. The emission maxima were at 329.6 nm and at 651.4 nm.

Figure 6B:
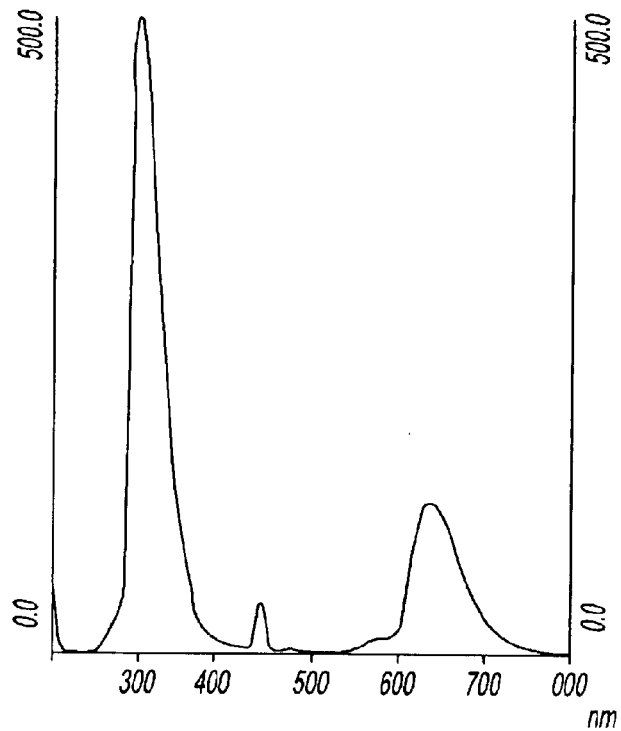

FIG. 6b Fluorescence spectroscopic profile of the cs-oxidant in methanol. The excitation was at 224 nm and emission scanning was measured from 225 nm to 800 nm. The emission maxima were at 329.6 nm and at 652.6 nm.

Figure 7A:
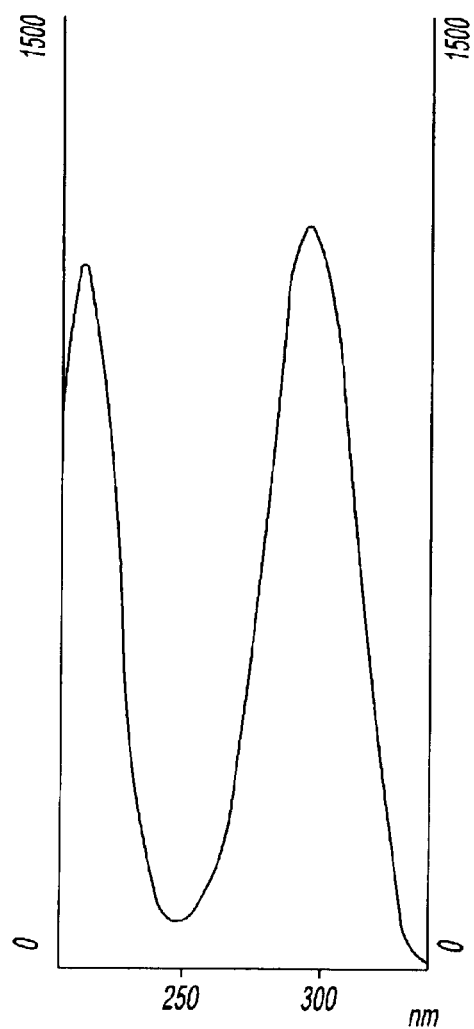

FIG. 7a Fluorescence spectroscopic profile of the cs-oxidant in methanol. The emission was at 330 nm and excitation scanning was measured from 220 nm to 325 nm. The excitation maxima were at 228.2 nm and 293.8 nm.

Figure 7B:
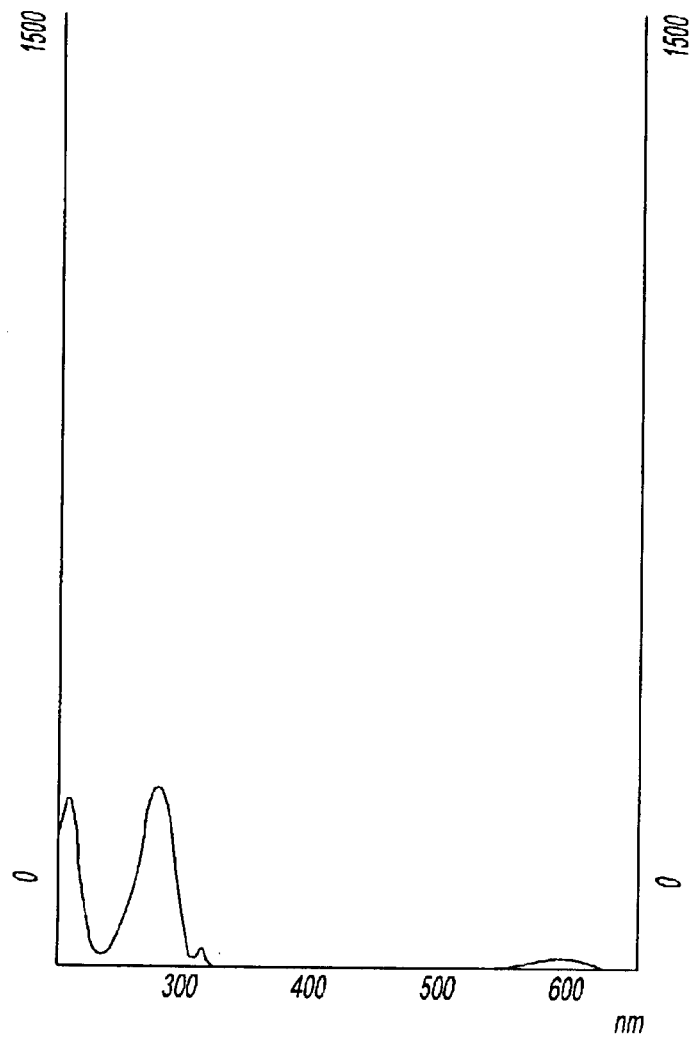

FIG. 7b Fluorescence spectroscopic profile of the cs-oxidant in methanol. The emission was at 651 nm and excitation scanning was measured from 220 nm to 650 nm. The excitation maxima were at 229.2 nm and at 294.8 nm.

Figure 8:
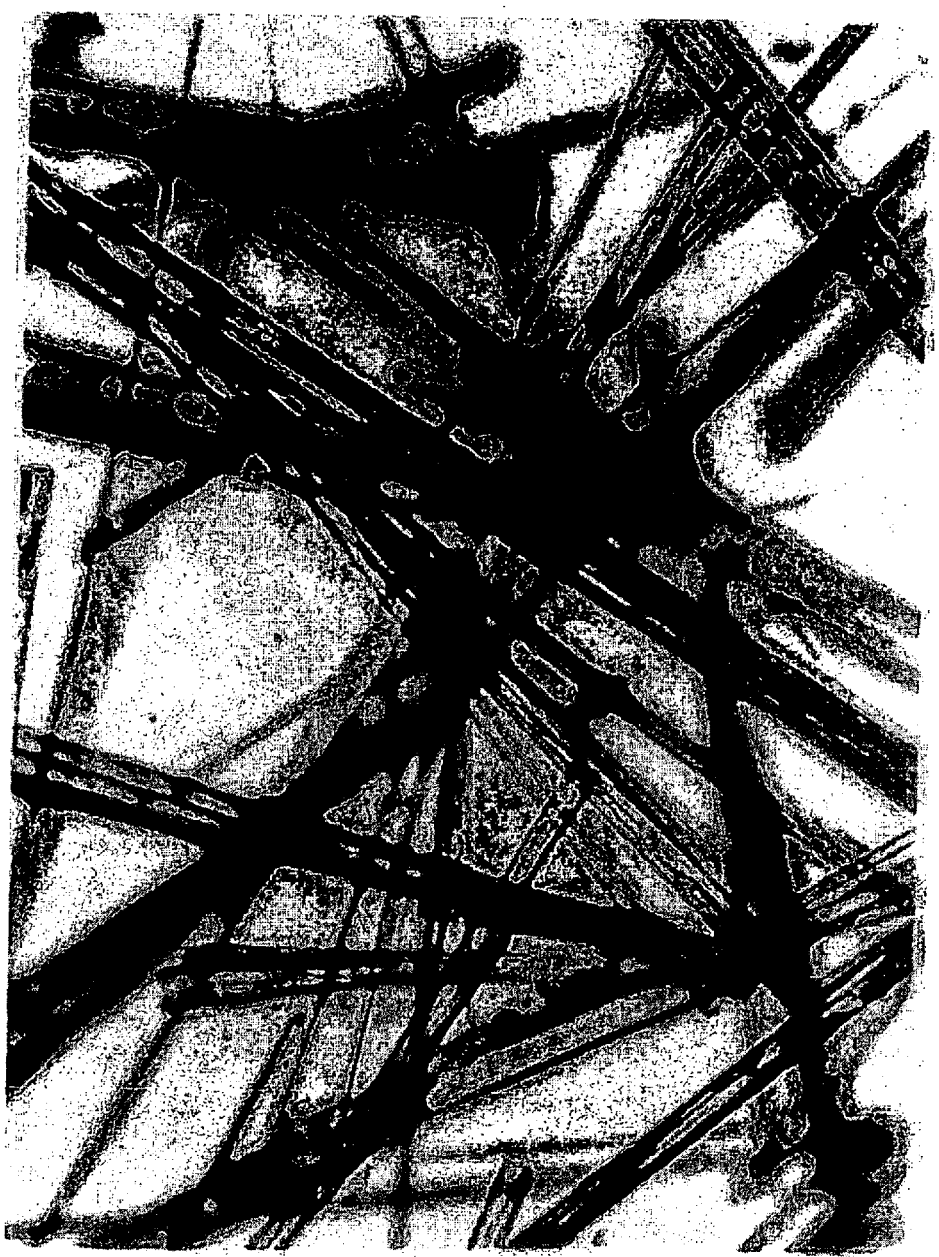

FIG. 8 Crystal structure of the pure cs-oxidant.

Figure 9:
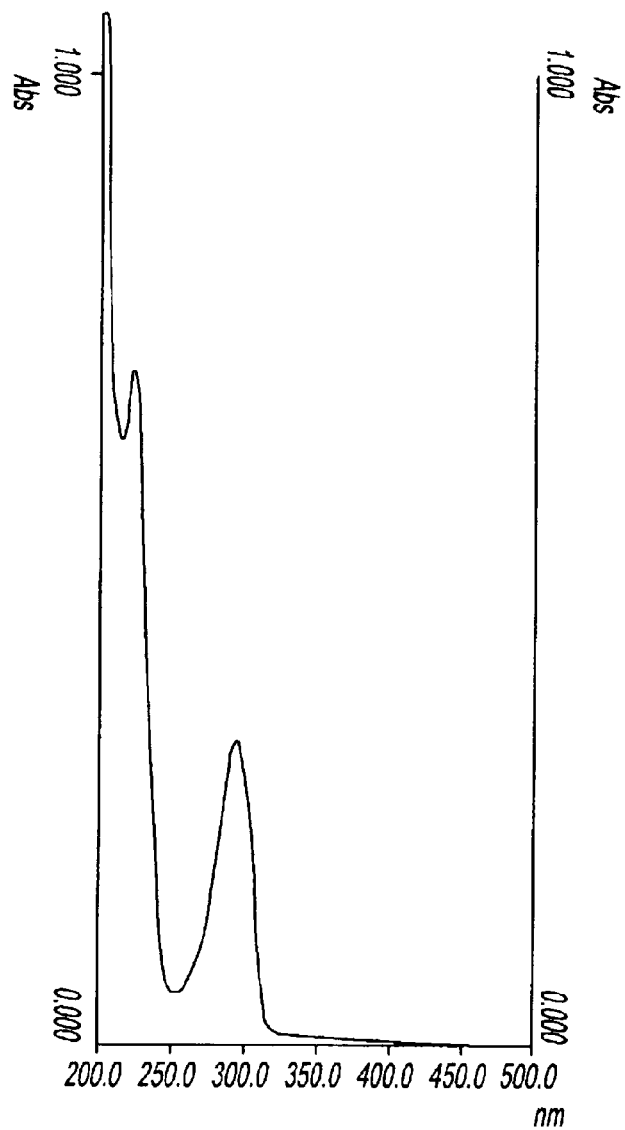

FIG. 9 UV-spectrophotometric profile of the cs-oxidant in methanol. It has two absorption maxima one at 293.4 nm and another at 223.0 nm.

Figure 10:
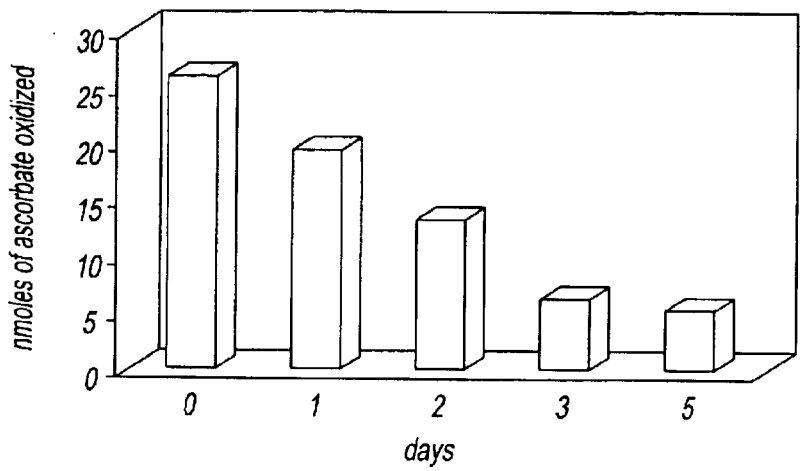

FIG. 10 Stability of the solid oxidant kept at 25° C. under darkness. The stability was determined by its capacity to oxidize ascorbic acid. Ascorbic acid was measured by HPLC analysis at 254 nm.

Figure 11:
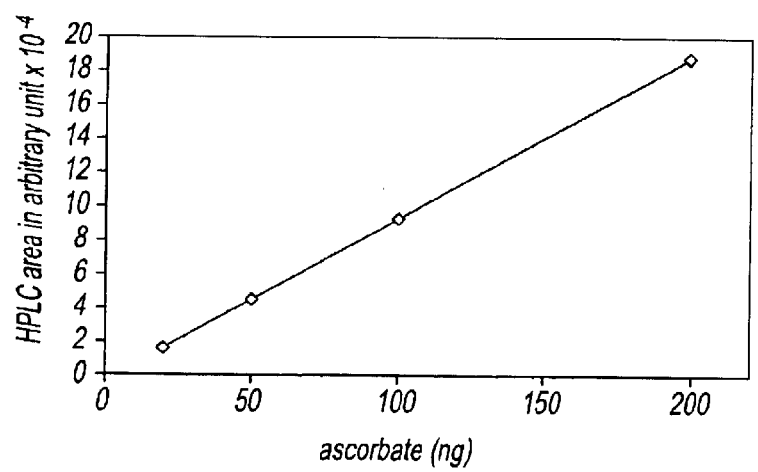

FIG. 11 Standard curve of ascorbic acid based on HPLC analysis at 254 nm.

Figure 12:
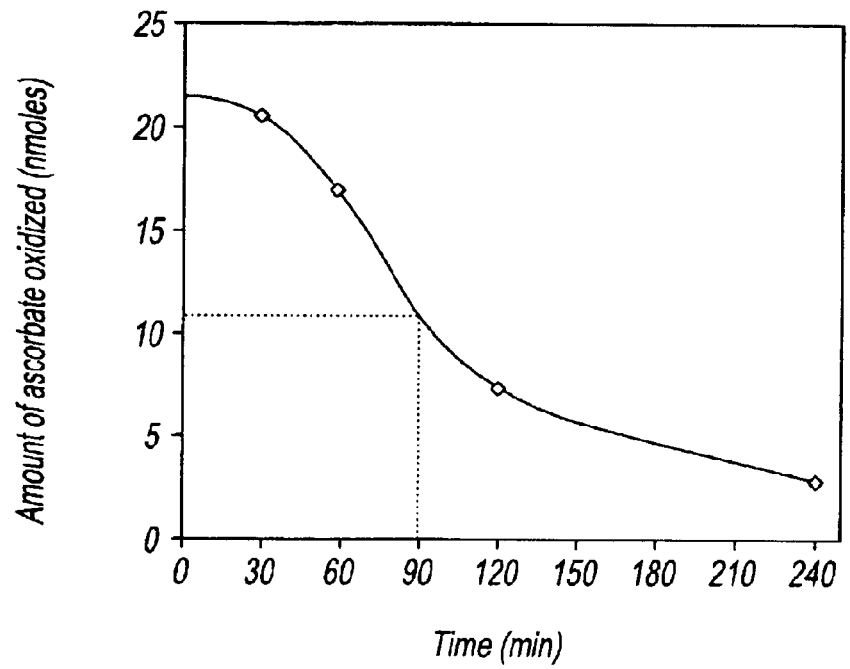

FIG. 12 Stability of the cs-oxidant in 50 mM potassium phosphate buffer at 25° C. measured by its potency to oxidize ascorbate as evidenced by HPLC area.

Figure 13:
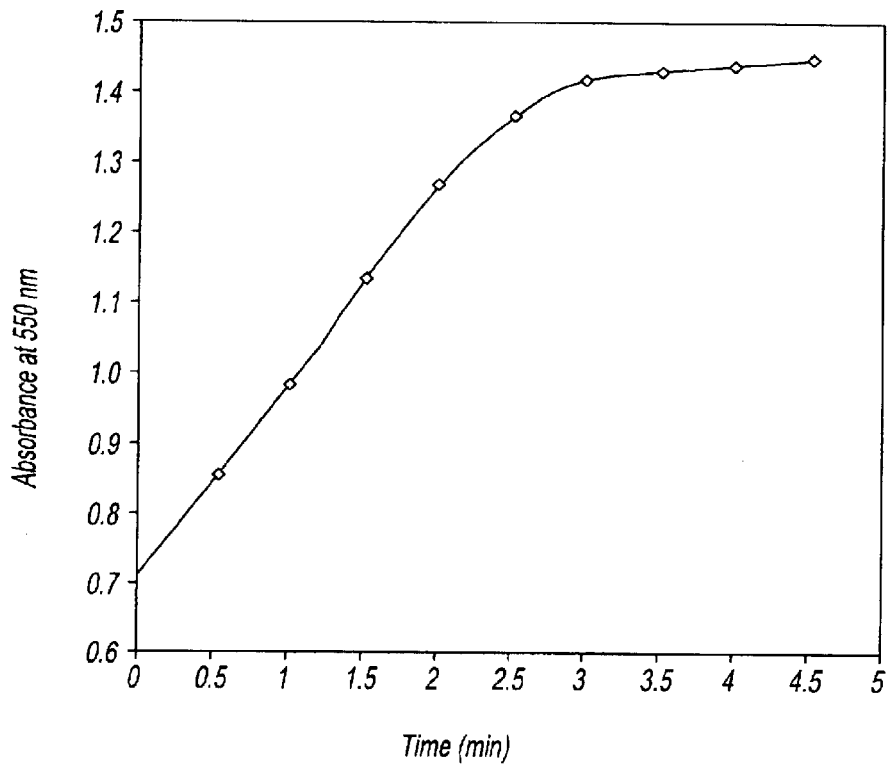

FIG. 13 Quantitative reduction of ferricytochrome c by the oxidant as measured by the formation of ferrocytochrome c with time at 550 nm. The reaction was carried out in 50 mM potassium phosphate buffer, pH 7.4, keeping the final concentration of ferricytochrome c at 100 $\mu$M. One nmole of the oxidant reduced 0.71 nmoles of ferricytochrome c.

Figure 14:
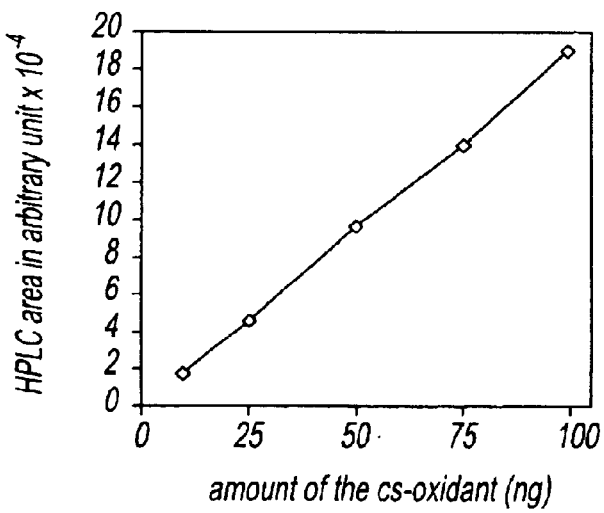

FIG. 14 Standard curve of the oxidant on the basis of HPLC area at 294 nm. Different amounts of the cs-oxidant were used ranging from 10 ng to 100 ng in 20 $\mu$l of mobile solvent.

Figure 15:
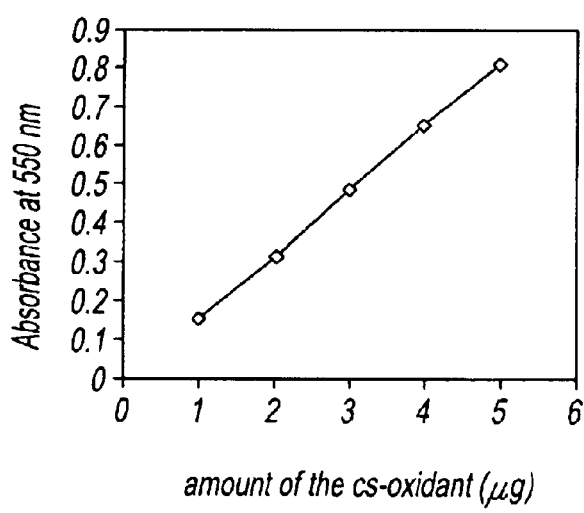

FIG. 15 Standard curve of the oxidant on the basis of reduction of cytochrome c by using different amount of the oxidant ranging from 1 $\mu$g to 5 $\mu$g.

Figure 16:
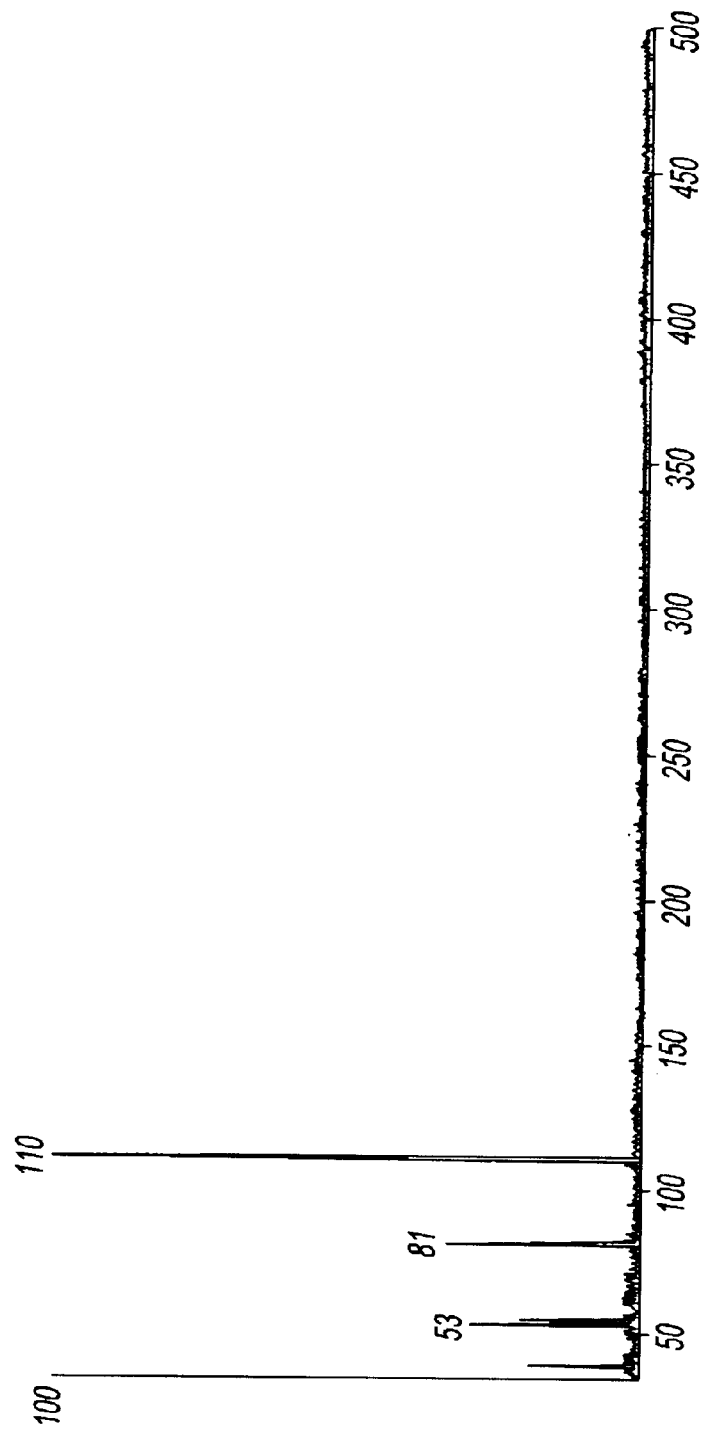

FIG. 16 Mass spectrum of the pure cs-oxidant.

Figure 17:
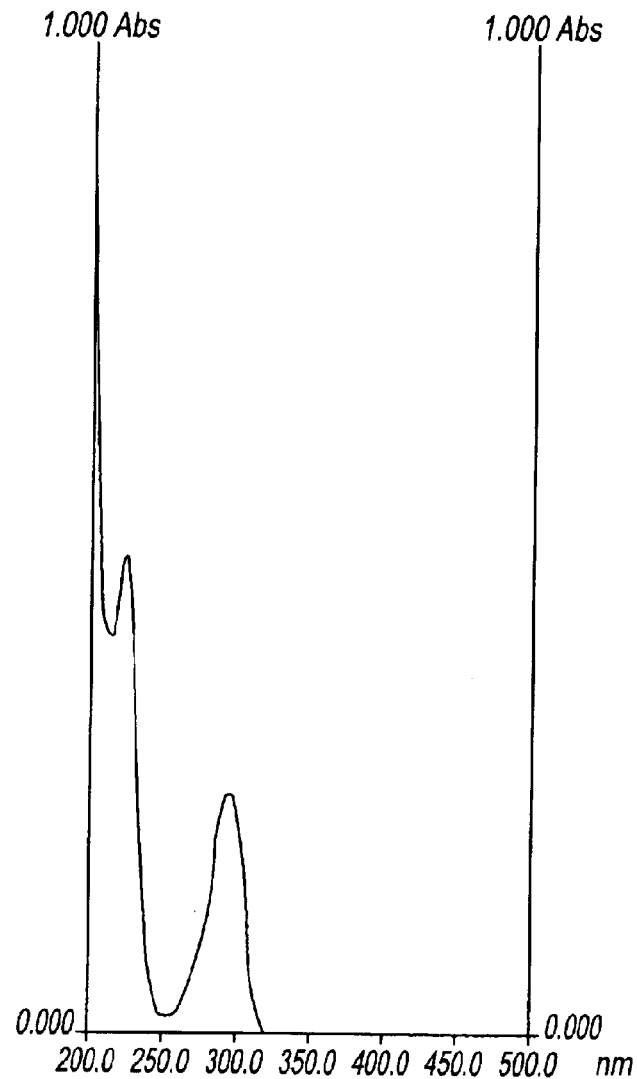

FIG. 17 UV-spectrophotometric profile of hydroquinone in methanol. It has two absorption maxima, one at 293.8 nm and another at 224.2 nm.

Figure 18:
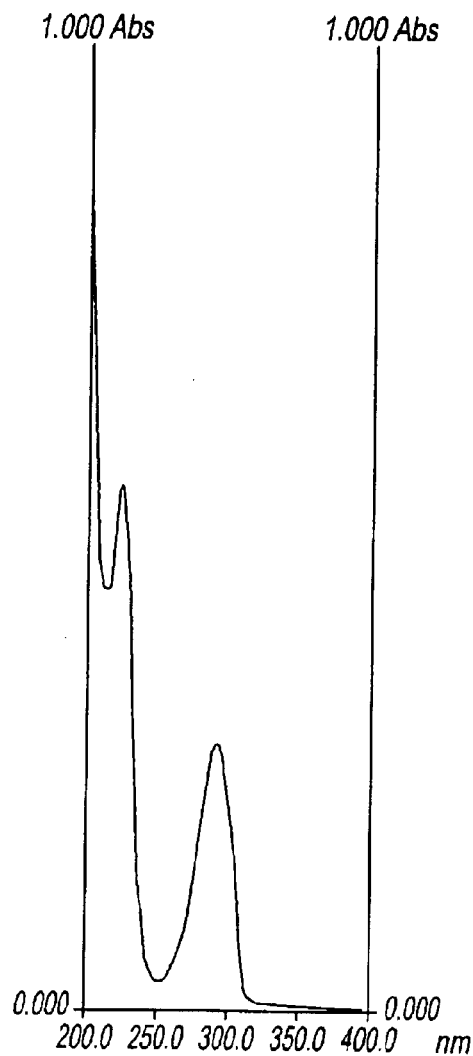

FIG. 18 UV-spectrophotometric profile of the cs-oxidant stored at room temperature in dark for 8 days. The two absorption maxima are at 293.6 nm and at 224.4 nm.

Figure 19:
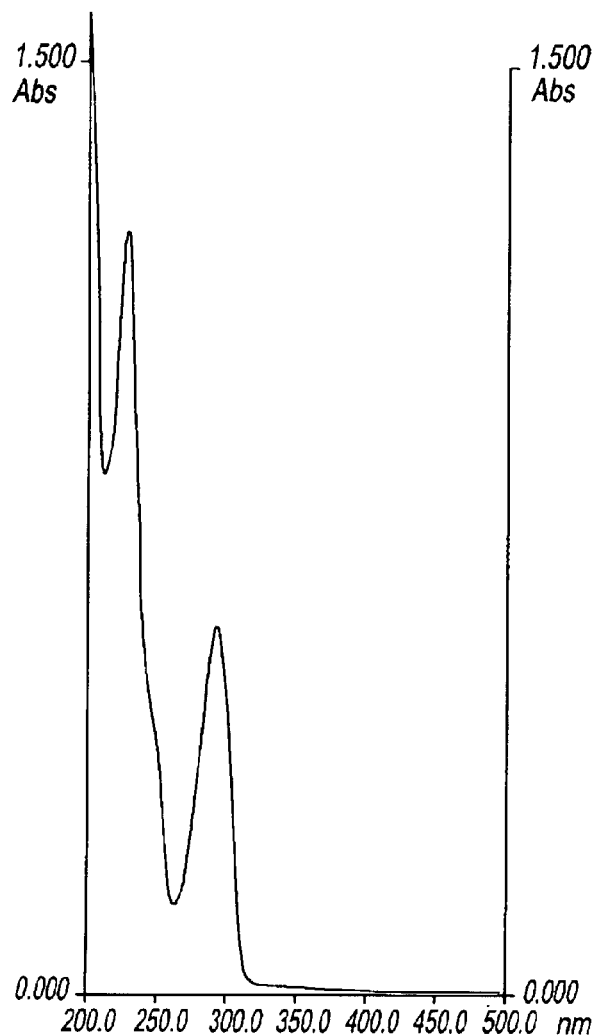

FIG. 19 UV-spectrophotometric profile of equimolar mixture of p-benzoquinone and hydroquinone in methanol. There is a shoulder near 242 nm (the $\lambda_{max}$ of p-benzoquinone).

Figure 20:
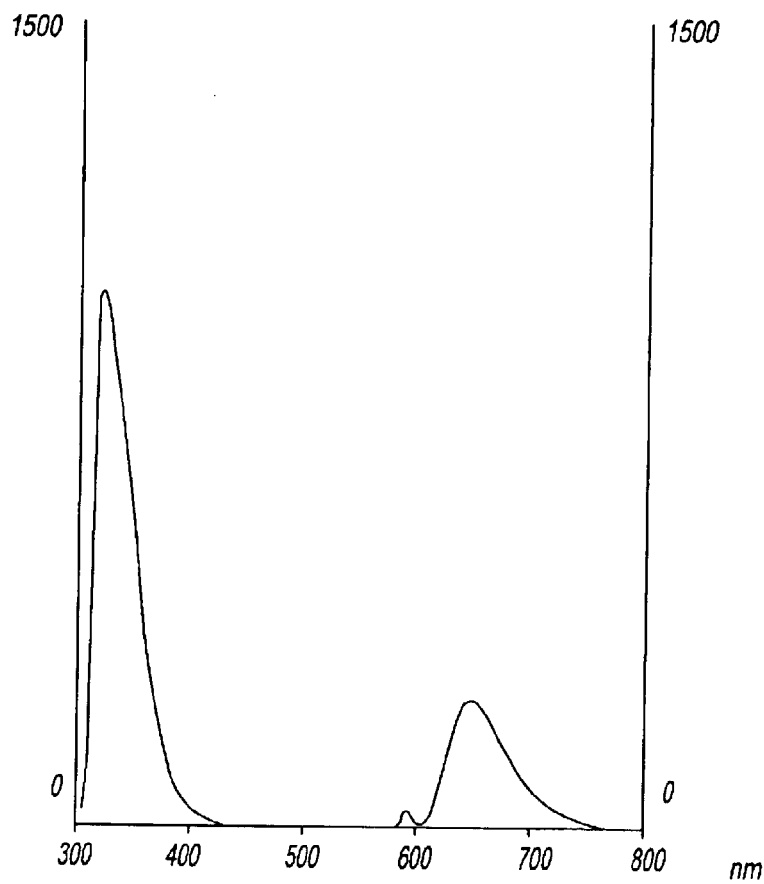

FIG. 20 Fluorescence spectroscopic profile of hydroquinone in methanol. The excitation was at 294 nm and emission scanning was measured from 300 nm to 800 nm. The emission maxima were at 329.4 nm and at 651.6 nm.

Figure 21:
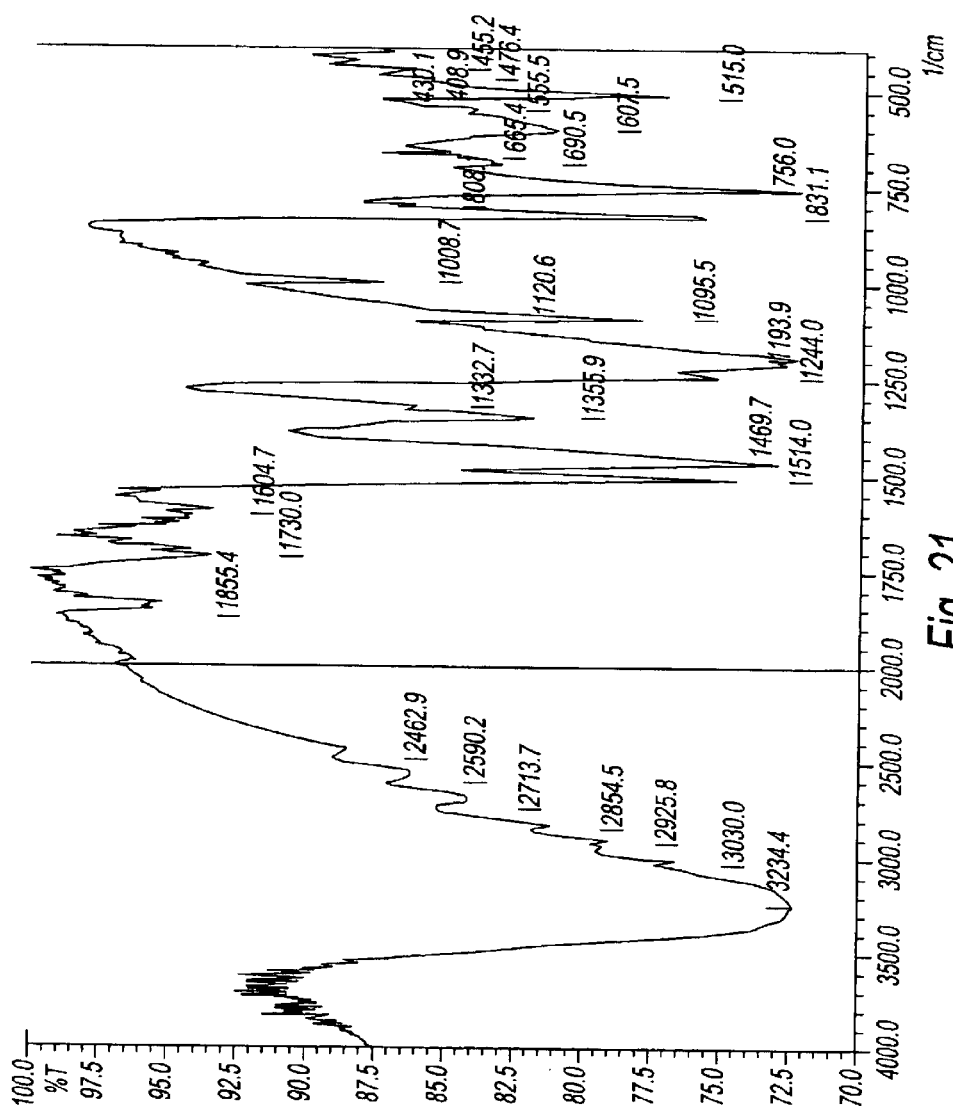

FIG. 21 FTIR spectroscopic profile of the cs-oxidant.

Figure 22:
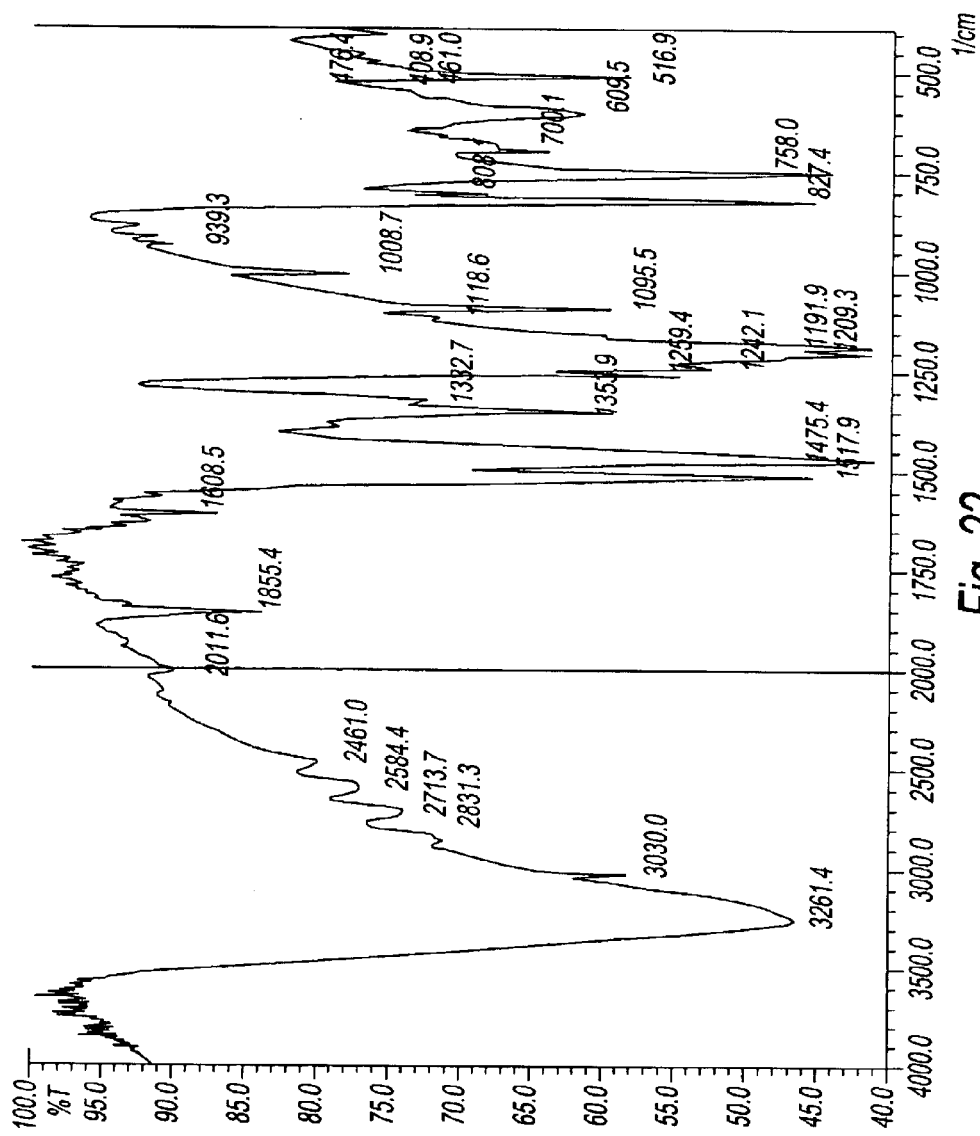

FIG. 22 FTIR spectroscopic profile of hydroquinone.

Figure 23:
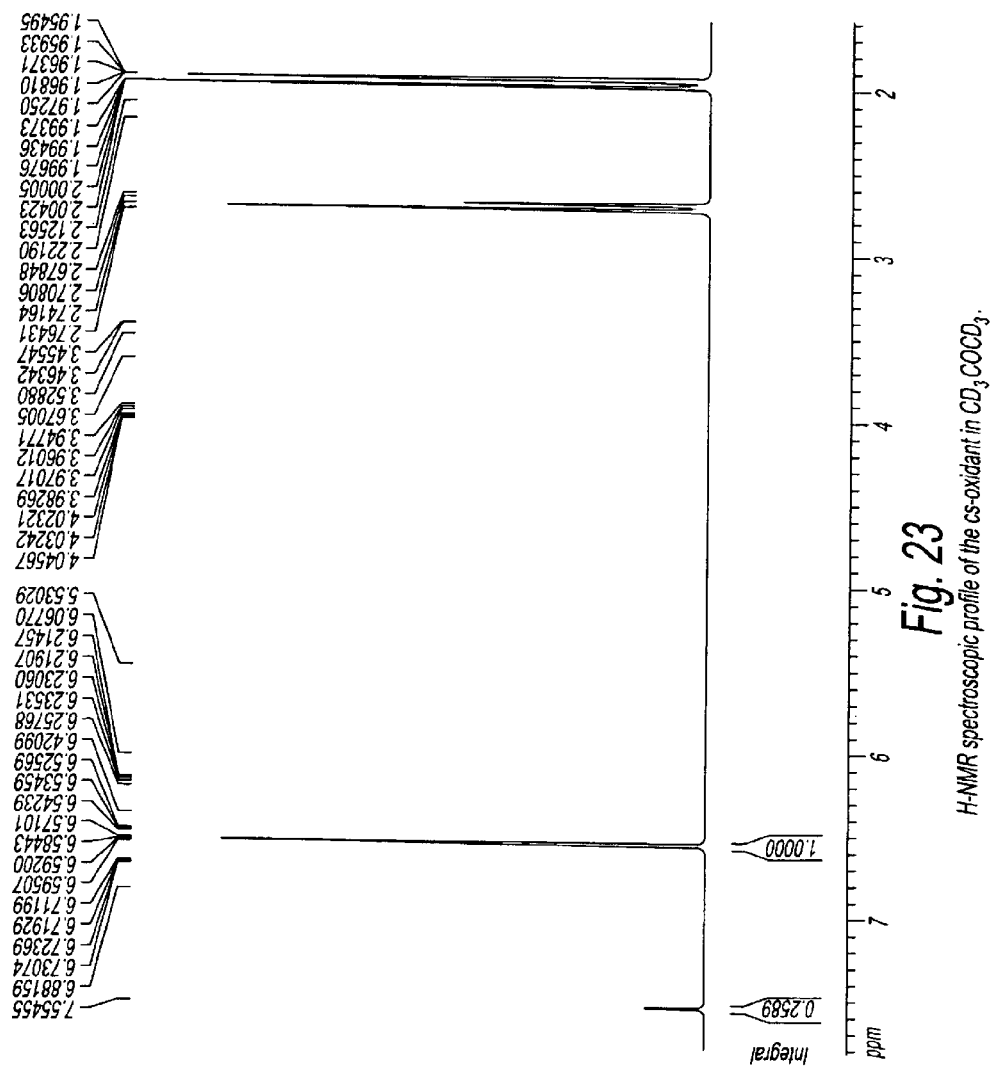

FIG. 23 H-NMR spectroscopic profile of the cs-oxidant in $CD_3COCD_3$.

Figure 24:
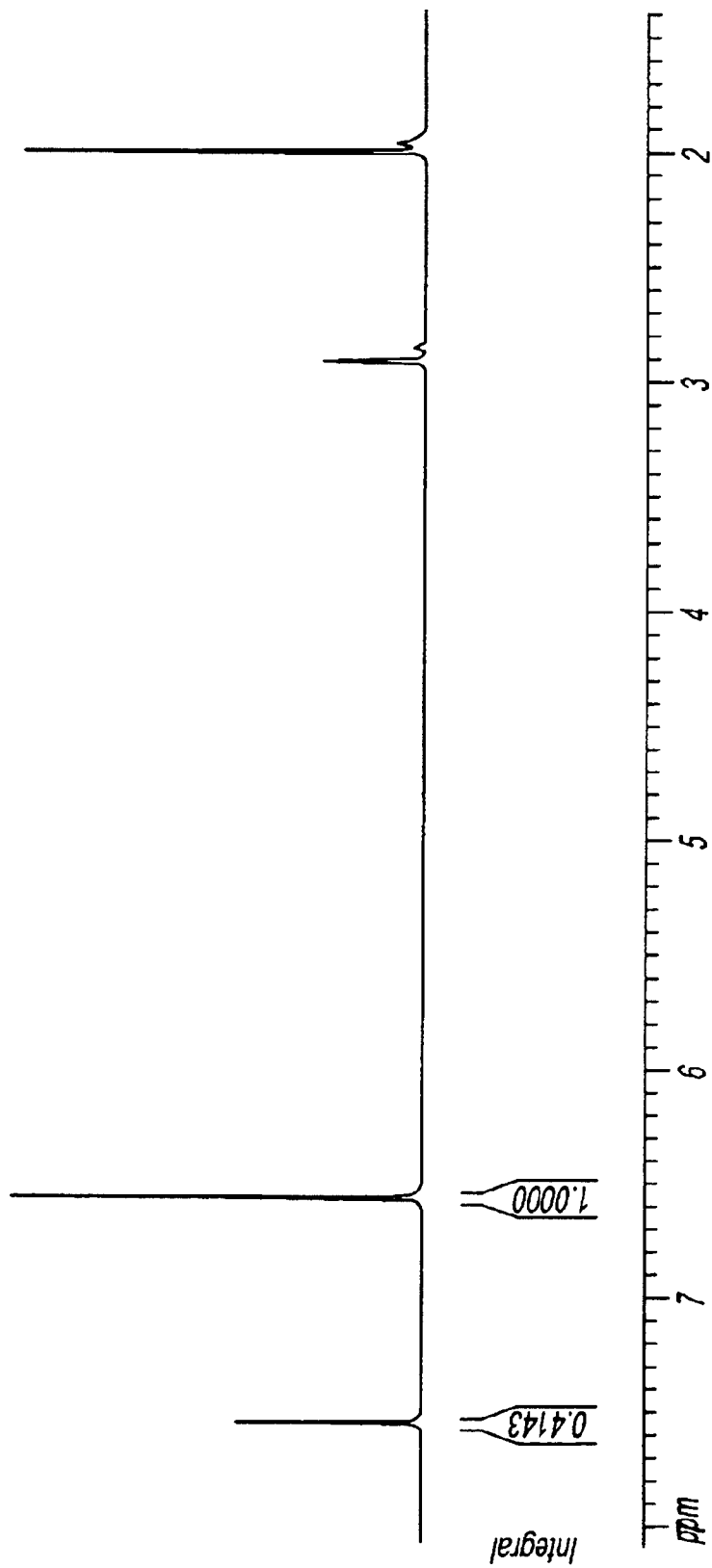

FIG. 24 H-NMR spectroscopic profile of hydroquinone in $CD_3COCD_3$.

Figure 25:
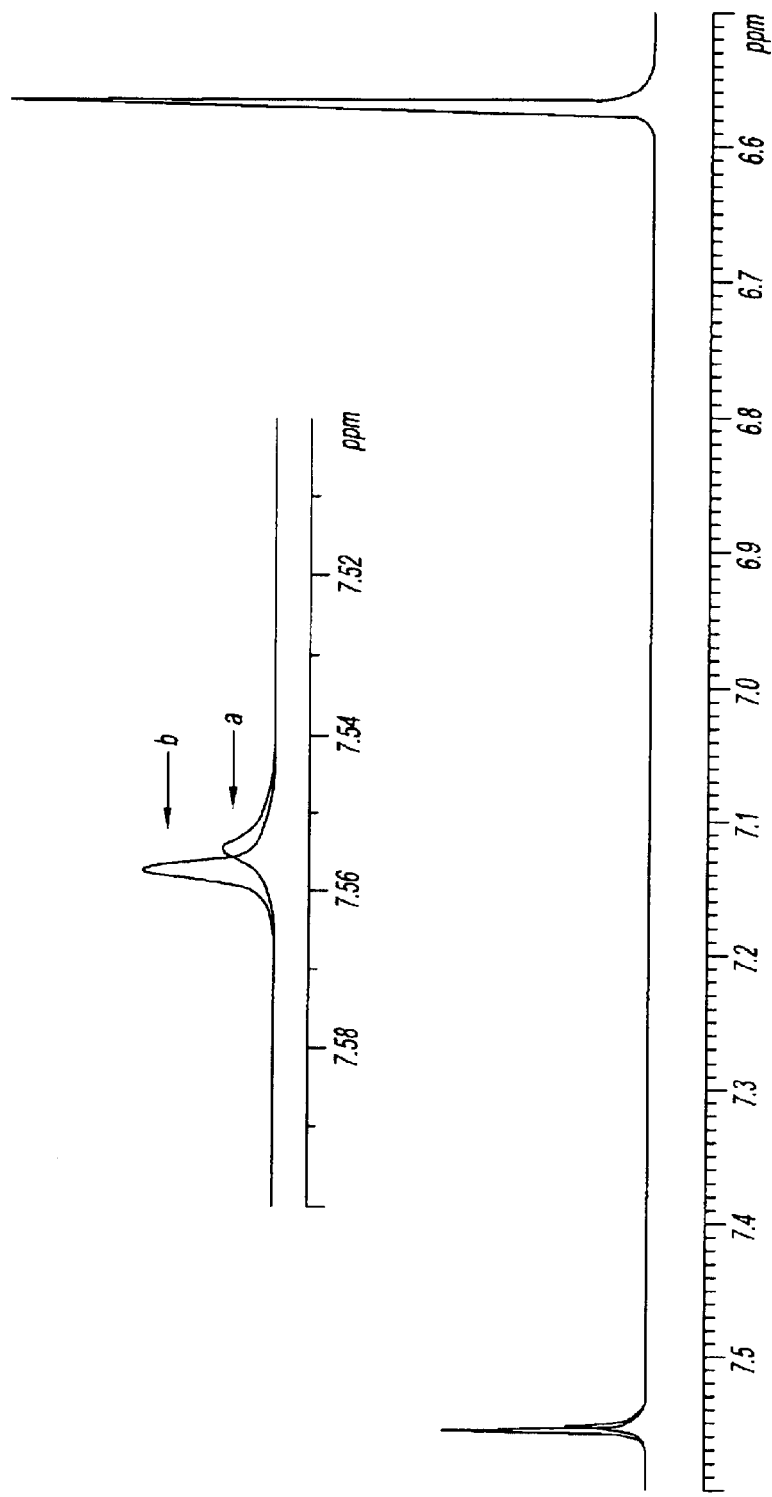

FIG. 25 Comparative H-NMR spectroscopic profiles of (a) cs-oxidant and (b) hydroquinone.

Figure 26:
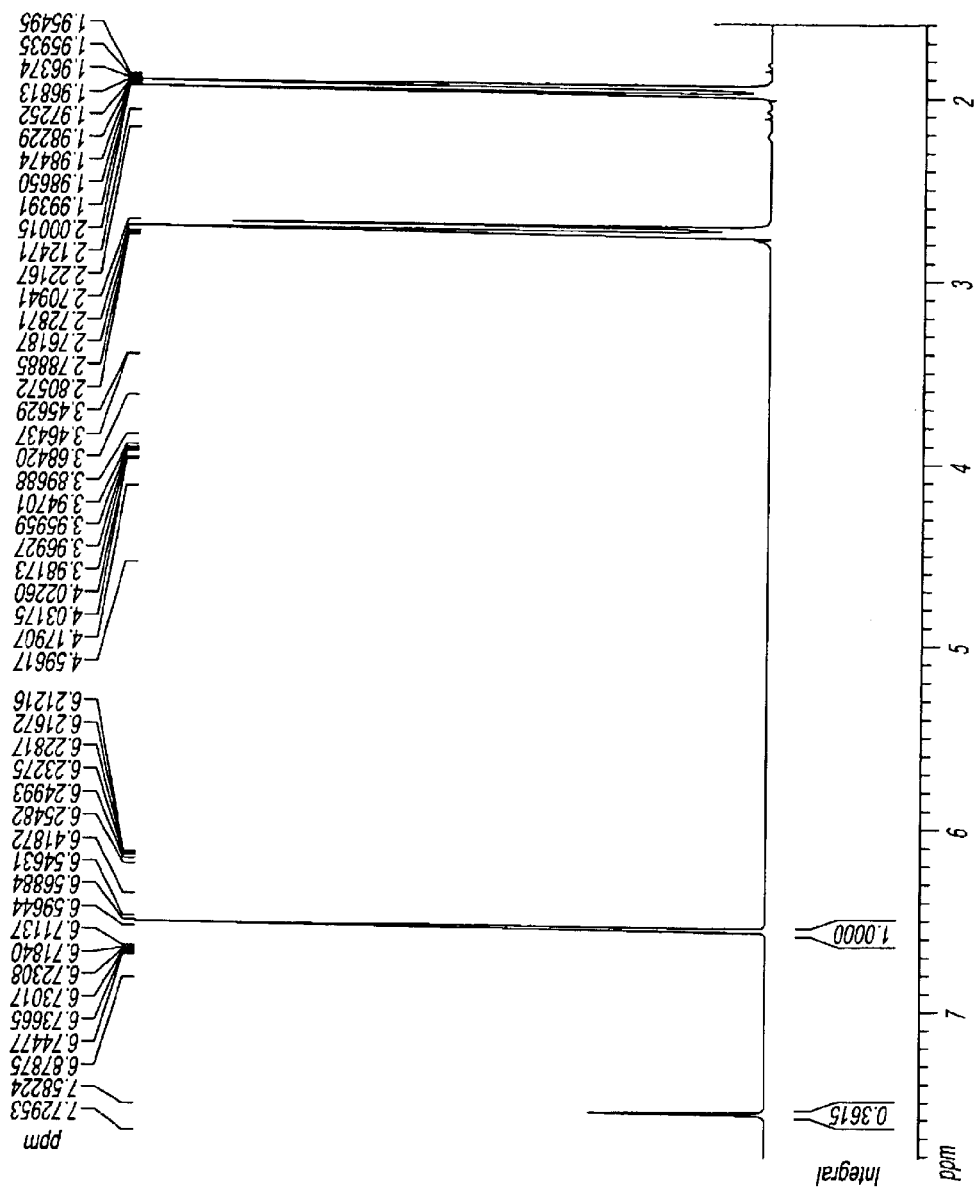

FIG. 26 H-NMR spectroscopic profile of the cs-oxidant after reduction with sodium dithionite.

Figure 27:
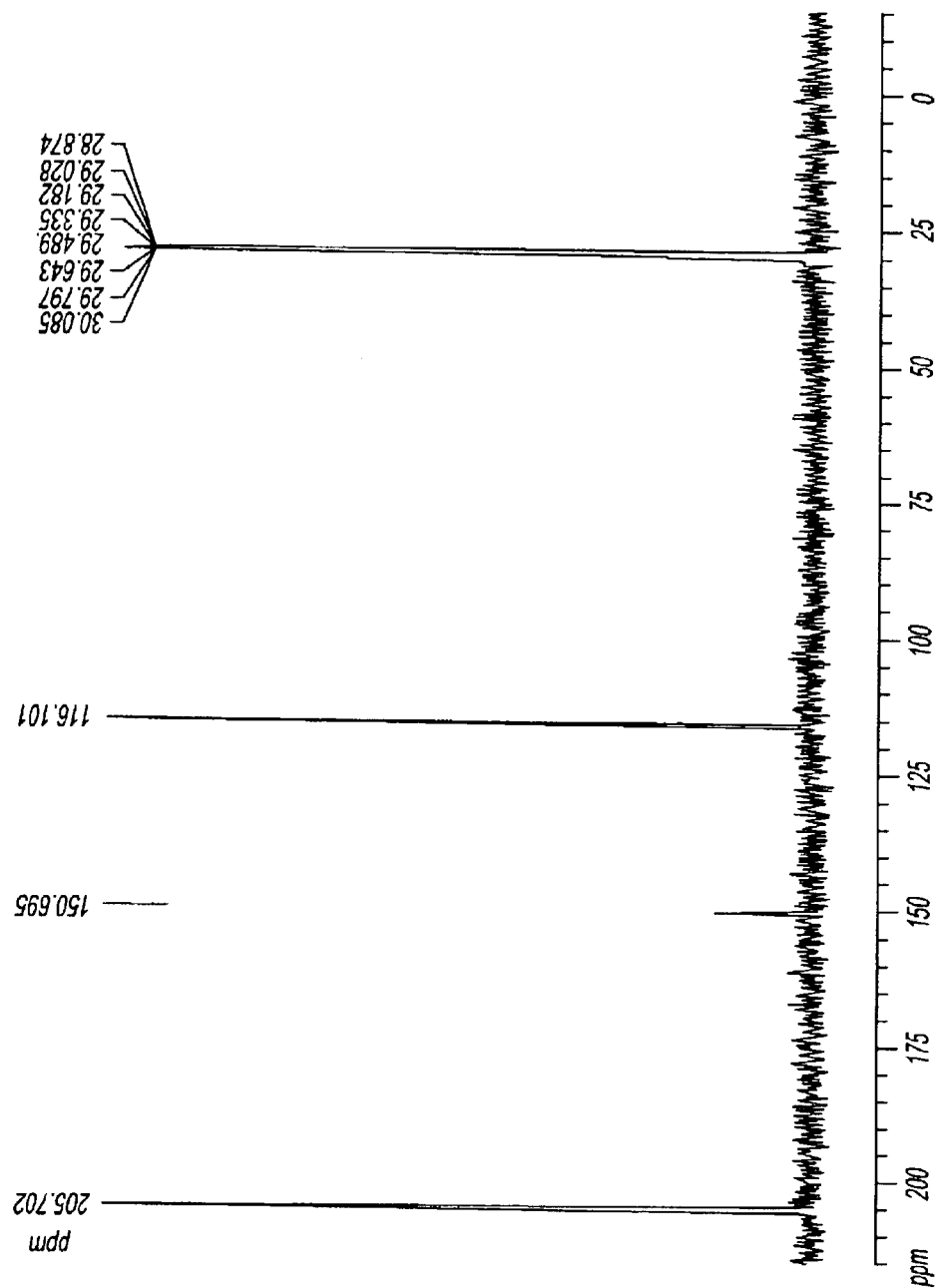

FIG. 27 C-NMR spectroscopic profile of the cs-oxidant in $CD_3COCD_3$.

Figure 28:
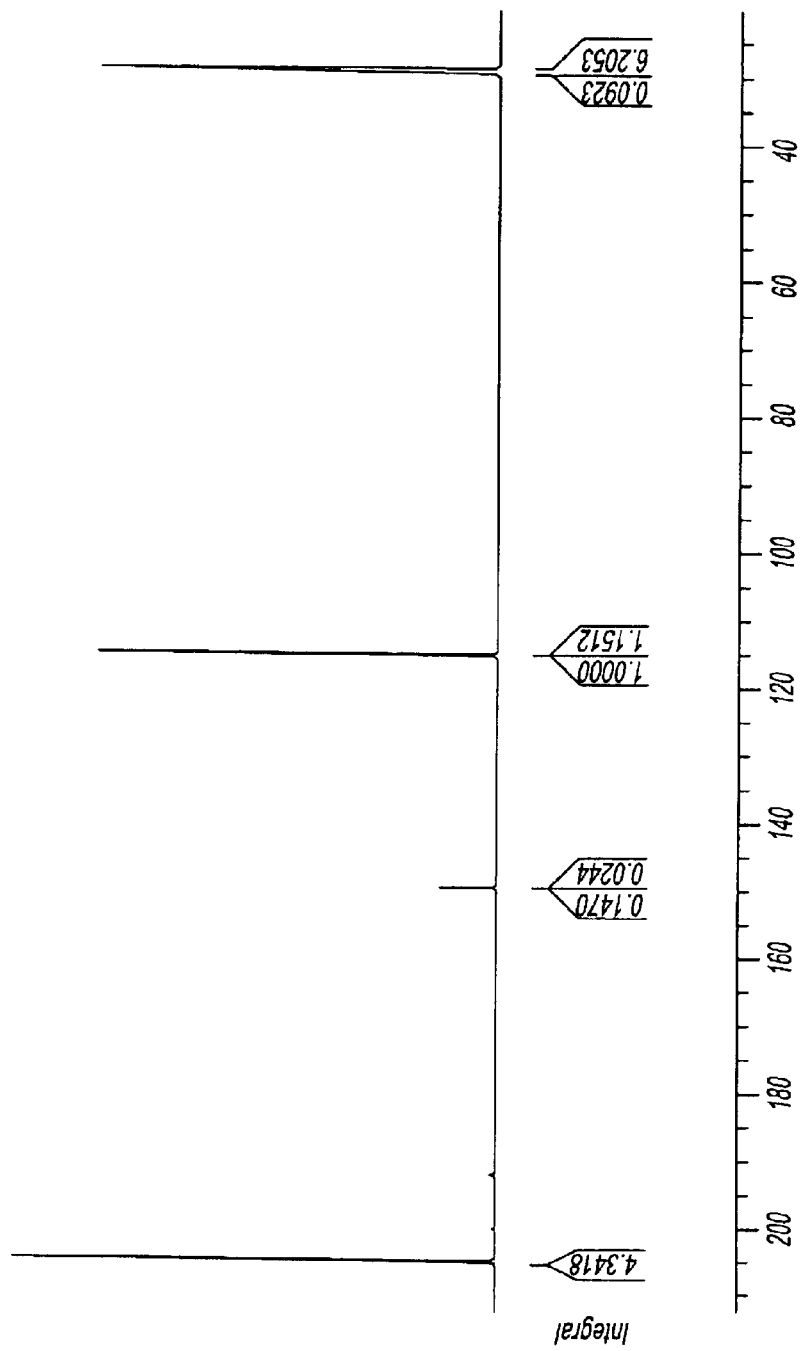

FIG. 28 C-NMR spectroscopic profile of the hydroquinone in $CD_3COCD_3$.

Figure 29:
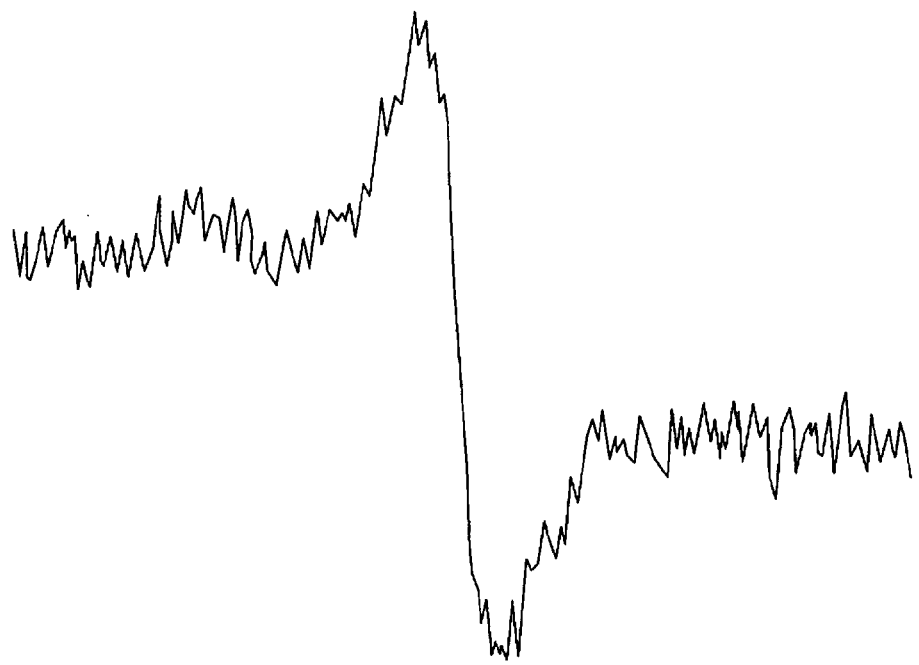

FIG. 29 Room temperature ESR spectrum of cs-oxidant, freshly prepared from 100 cigarettes. The spectrum was recorded on a JES-REIX ESR spectrometer (Tokyo, Japan). The spectral parameters were as follows: microwave frequency, 9.4356 GHz; power, 2 mW; field modulation width, 0.4 mT; modulated frequency, 100 kHz; time constant, 0.3 sec; scant rate, 2.5 mT/sec.

Figure 30:
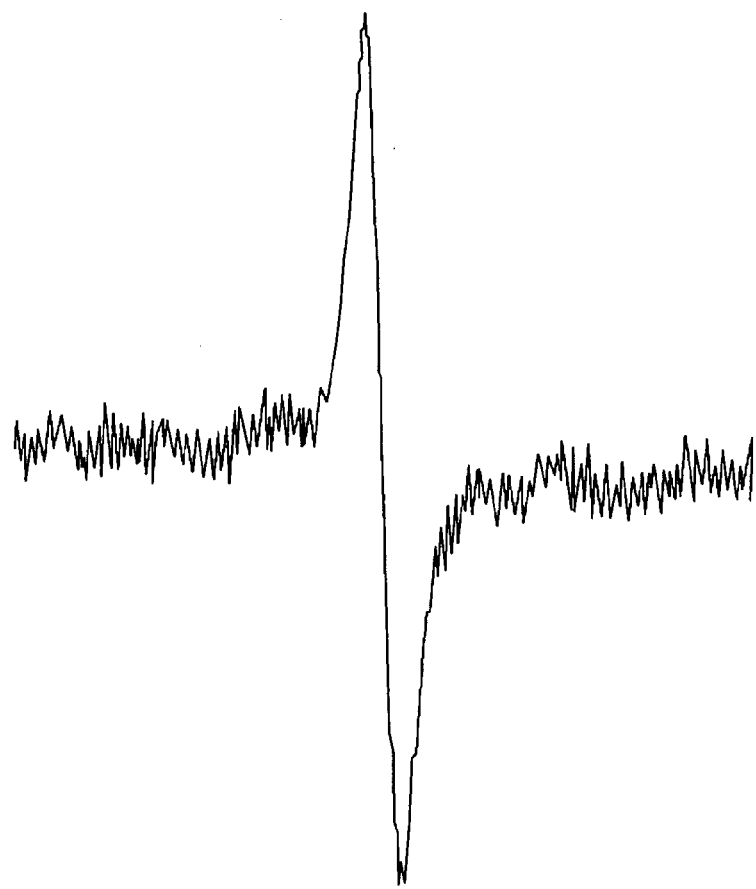

FIG. 30 Room temperature ESR spectrum of aged (10 days) cs-oxidant, prepared from 400 cigarettes.

Figure 31:
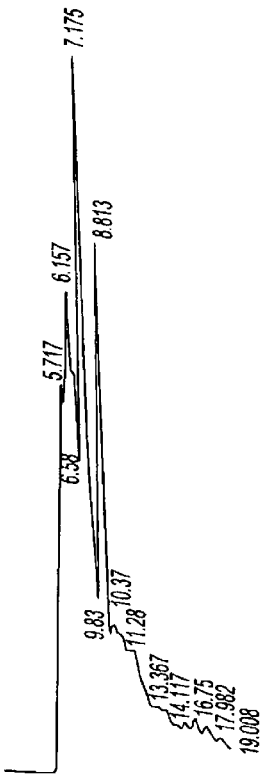

FIG. 31 HPLC profile of the whole cs solution analyzed in the silica column (LiChrospher® Si 60,Merck)—indicates the retention time, area and the concentration (13.6682%) of the cs-oxidant.

Figure 32:
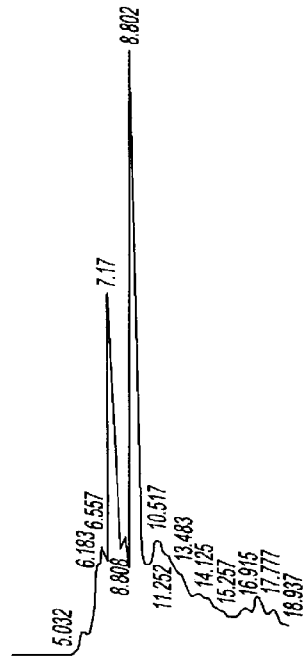

FIG. 32 HPLC profile of the aqueous extract cs solution analyzed in the silica column (LiChrospher® Si 60,Merck)—indicates the retention time, area and the concentration (13.6682%) of the cs-oxidant.

Figure 33:
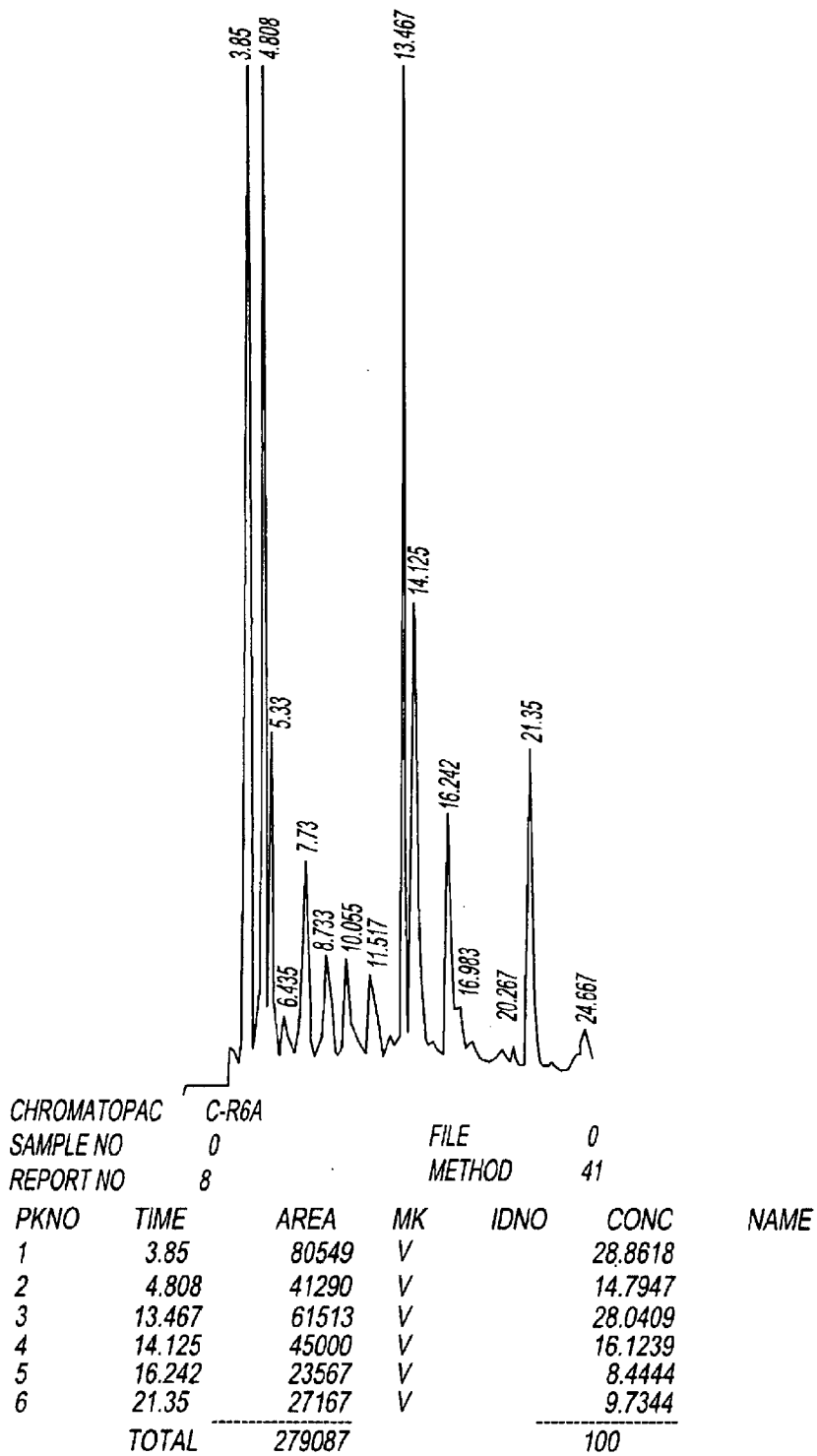

FIG. 33 HPLC profile of the whole cs solution analyzed in the ODS column (Shim-pack CLC-ODS, Shimadzu). The cs-oxidant eluted at 13.467 min.

Figure 34:
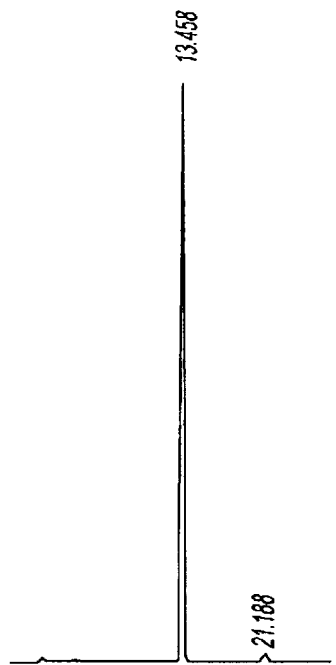

FIG. 34 HPLC profile of the pure-cs-oxidant analyzed in the CLC-ODS column (Shim-pack CLC-ODS, Shimadzu) eluted at the retention time of 13.458 min.

FIG. 35a SDS-PAGE of the quinea pig lung microscomal proteins treated with whole cs solution and the cs-oxidant Lane 1, untreated microsomes; lane 2, microsomes treated with 50 $\mu$l cs solution; lane 3, microsomes treated with 100 $\mu$l cs solution; lane 4, microsomes treated with 10 $\mu$g cs-oxidant; lane 5, microsomes treated with 20 $\mu$g cs-oxidant.

FIG. 35b Densitometric scanning of the protein bands of different lanes as in FIG. 35a.

DETAILED DESCRIPTION OF TABLES

Table 1. Estimation of oxidative potency at different stages of purification of the cs-oxidant Table 2. Oxidation of ascorbic acid by the cs-oxidant as measured by HPLC analysis Table 3. BSA oxidation by fractions of CS-solution at different stages of purification Table 4. Protection of cs-oxidant-induced albumin oxidation of different chemical agents.

Table 5. Inactivation of the major harmful cs-oxidant and nicotine delivery in cigarette smoke using activated charcoal filter

EXAMPLES

Example 1

Isolation and Purification of a Major Hazardous Component (cs-oxidant) from Cigarette Tar or Whole Cigarette Smoke Solution (i). Five Indian commercial filter-tipped cigarette (74 mm) with a tar content of 25 mg each was mounted in glass tubes that penetrated the hole in the glass stopper of a one liter glass Erlenmeyer flask with a side arm and ended about 2 cm away from the bottom of the flask. The flask was dipped in a mixture of ice and salt and the side arm connected to a water pump. The cigarettes were lit and the tar was allowed to condense and settle at the bottom of the flask. Altogether tar from twenty cigarettes was collected. The jar was taken out to room temperature and the tar was extracted with 20 ml of 50 mM potassium phosphate buffer pH 7.4. The solution was filtered through 0.45 $\mu$m Millipore filter. The pH of the filtrate was adjusted to 7.4 with addition of 20 $\mu$l of 2N NaOH solution. The colour of the solution was brownish yellow. This solution has been termed tar solution.

Instead of isolating the cs-oxidant from cigarette tar, it can also be isolated from whole cigarette smoke. In that case, smoke from 20 cigarettes in batches of 5 is passed directly into 20 ml of 50 mM potassium phosphate buffer, pH 7.4, and the rest of the procedure is similar to that used in tar. The solution obtained after passing the whole cs into the buffer has been termed whole cs solution. The yield of the cs-oxidant was similar irrespective of whether the tar solution or whole cs solution was used as the starting material.

(ii) The filtered tar solution obtained in step 1 was extracted thrice with 15-ml methylene chloride. The lower methylene chloride layer was discarded and the upper yellow coloured aqueous layer was collected and called the aqueous extract of cigarette smoke.

(iii) The aqueous layer from step 2 was extracted twice with 10 ml of water saturated n-butanol and the pooled yellow butanol extract was then lyophilized in the Lyolab lyophilizer at −55° C. under vacuum. The lyophilized material was extracted twice with 1 ml of HPLC grade acetone and the acetone solution was dried in a Speed Vac (Savant, SC 100) and dissolved in 120 $\mu$l of HPLC grade methanol.

(iv) The methanol solution obtained in step 3 was then subjected to band TLC using 10-cm×10 cm non-fluorescent 0.2-mm thick silica plates (TLC aluminium sheets, Silica gel 60, MERCK, No 1.05553) Material from 5 cigarettes (≈30 $\mu$l methanol solution) was spotted along a line about 1.5 cm above the bottom. The plate was developed using toluene: ethyl acetate (80:20) for 15 min. When the developing solvent front was 0.5 cm away from the top, the plate was taken out and dried at room temperature using a drier After drying, 0.5 cm strips from both the right and the left side of the plate was cut out and kept in a iodine chamber for 3 minutes for location of the bands. The band corresponding to Rf 0.26 (FIG. 2) was scraped from each plate, taken in 1.5 ml eppendorf tube and extracted for 30 min with 600 $\mu$l HPLC grade acetone with occasional vortexing. The tubes were then centrifuged for 10 min at room temperature at 12000 rpm. The supernatant acetone layer was carefully taken in another eppendorf tube. The pooled acetone extract was finally dried in one eppendorf tube in a speed vac.

(v) To the dried material obtained in step 4, which appeared as pale yellow needles, was added 200 $\mu$l milli Q water and to this 200 $\mu$l water saturated n-butanol was added and vortexed for 5 min followed by centrifugation for 5 min at 12000 rpm at room temperature. The upper n-butanol layer was carefully taken out and dried in a small glass tube in a speed vac.

Yield≈400 $\mu$g from 20 cigarettes. At this stage, the cs-oxidant is 98.5% pure as evidenced by HPLC analysis.

(vi) The total sample obtained after step 5 was dissolved in 400 $\mu$l of the mobile solvent and 20 $\mu$l of this solution (≈20 $\mu$g oxidant) was injected in a Shimadzu 10AVP HPLC instrument with a normal phase Merck 25 cm silica column (LiChrospher® Si 60) using the UV detector and an attached chromatopac C-R6A. Altogether 20 injections were made in different batches.

The other conditions maintained were as follows.

Absorbance: 294 nm (The $\lambda_{max}$ of the oxidant in methanol was 293.4 nm as evidence by UV-spectrophotometric scanning, see FIG. 9)

Mobile solvent:methylene chloride:methanol (90:10)

| Flow rate: | 0.5 ml/min |
|---|---|
| Pressure: | 29 kgf/cm$^2$ |
| Temperature: | 25° C. |
| Retention time of the oxidant: | 8.808 min |

The oxidant eluted as a major peak at retention time of 8.808 min (FIG. 3). The pooled HPLC effluent obtained from different batches of injection was collected in a 25-ml glass beaker and dried in the speed vac. The oxidant appeared as very-faint yellow tiny needle-shaped crystals. The HPLC-purified oxidant, when reinjected under identical conditions, appeared as a single peak in the HPLC profile at a retention time of 8.808-min (FIG. 4), indicating 100% purity.

Yield≈300 $\mu$g from 20 cigarettes.

(vii) On the basis of the amount of sample loaded and the corresponding peak area (arbitrary) of the cs-oxidant obtained in HPLC analysis, the percentage recovery of the active oxidant from the whole cs solution was calculated as follows.

Four $\mu$l of the filtered whole cs solution (see step 1) was diluted to 80 $\mu$l with mobile solvent and 20 $\mu$l was injected in the HPLC column.

The arbitrary area of the oxidant in 20 $\mu$l, corresponding to retention time 8.808 min, was 340583.

Therefore, area in 80 $\mu$l=1362332=4 $\mu$l of whole cs solution.

So, arbitrary area of the oxidant in one ml of whole cs solution=3.4×10$^8$.

Since one ml of the whole cs solution is equivalent to one cigarette (see step 1), the area of the cs-oxidant per cigarette=3.4×10$^8$.

The yield of pure oxidant after HPLC purification from 20 cigarettes=300 $\mu$g.

So, yield from one cigarette=15 $\mu$g=15000 ng.

From the standard curve (see FIG. 14), HPLC peak area of 100 ng of pure cs-oxidant=190000.

Therefore, peak area of 15000 ng, equivalent to one cigarette=2.85×10$^7$.

Thus the recovery of the pure cs-oxidant from whole cs solution is (2.85×10$^7$×100)/3.4×10$^8$=8.4%.

(viii) The oxidative potency of the cs-oxidant at different stages of purification was determined by measuring the oxidation of bovine serum albumin (BSA). The results are presented as nmoles of protein carbonyl formed per mg BSA (Table 1). At different stages of purification, as stated under 'Isolation and purification procedure' above, an amount of material equivalent to one twentieth of a cigarette (50 $\mu$l solution) was used in the cases of tar solution (step 1), aqueous extract (step 2) and butanol extract (step 3). In the case of butanol extract, 50 $\mu$l of the butanol solution was taken, butanol evaporated off in a speed vac, the dried residue weighed and used directly for the oxidation of BSA. For materials obtained at step 4 (TLC) and step 6 (HPLC), the amounts used were 15 $\mu$g and 10 $\mu$g respectively.

(ix) Criteria of purity of the cs-oxidant (a) TLC: A single spot was obtained in TLC, R$_f$ 0.26, using toluene:ethyl acetate (80:20) as the developing solvent (FIG. 5).

(b) HPLC: A single peak was obtained by HPLC analysis. The retention time was 8.808 min using the mobile solvent, methylene chloride:methanol (90:10) (FIG. 4).

(c) Melting point: The compound melts sharply at 162° C.

(d) Fluorescence spectroscopy:

The UV spectrophotometric scanning of the cs-oxidant (5 mg in 1 ml of methanol) produced two absorption maxima at 293.4 nm and at 223.0 nm (see FIG. 9). Fluorescence spectroscopy was performed in methanol solution as used for UV spectrophotometric scanning. When excited at 293 nm, the emission scanning was monitored from 300 nm to 800 nm and when excited at 224 nm, the emission scanning was monitored from 225 nm to 800 nm. When excited at 293 nm, the observed emission maxima were at 329.6 nm and 651.4 nm (FIG. 6*a*). When excited at 224 nm, the observed emission maxima were at 329.6 nm and at 652.6 nm (FIG. 6*b*). When excitation scanning was monitored keeping the emission at 330 nm, the observed excitation maxima were at 228.2 nm and at 293.8 nm (FIG. 7*a*). Again, when the emission was kept at 651 nm and excitation scanning was monitored, the observed excitation maxima were at 229.2 nm and at 294.8 nm (FIG. 7*b*).

The observed spectral profiles indicate that the two absorption maxima are coming from the same compound and attributes to the purity of the isolated cs-oxidant.

Example 2
Quantitative Assay of Protein Damage by Measuring Carbonyl Content.

The incubation system contained 1 mg BSA and 50 µl of cs solution or its equivalent amounts obtained at different stages of purification in a final volume of 200 µl of 50 mM potassium phosphate buffer, pH 7.4. The incubation was carried out at 37° C. for 1 hour. Protein carbonyl was measured by reaction with 2,4-dinitrophenyl hydrazine (DNPH) following the method of Levine et al (Methods Enzymol. 186: 464–478, 1990) similar to that done before in our laboratory (Panda et al., Free Radic. Biol. & Med. 27: 1064–1079, 1999). After incubation of BSA with whole phase cs solution, the aqueous extract of cs or the cs-oxidant (final volume 200 µl), the proteins were precipitated with 200 µl of 20% trichloroacetic acid solution followed by a wash with 200 µl of 10% trichloroacetic acid solution to free the pellet of cs components. To this washed pellet was then added 500 µl of 10 mM DNPH solution in 2M HCl and incubated at 37° C. for 1 h with occasional vortexing. Thereafter, the protein was again precipitated with 500 µl of cold 20% trichloroacetic acid solution and the pellet was first washed with 500 µl of 10% trichloroacetic acid solution followed by three successive washes with 1 ml of a mixture of ethanol:ethyl acetate (1:1, v/v). Finally, the washed precipitate was dissolved in 1 ml of 6M guanidium hydrochloride (pH 2.3) and the absorbance was measured at 390 nm using a double beam Hitachi spectrophotometer model U 3020 against a reagent blank of 2M HCl. The results were expressed as n moles of phenylhydrazones formed per milligram protein using a molar extinction coefficient of 22,000. From the gross phenylhydrazone values obtained after incubation of BSA with the cs-oxidant, the phenylhydrazone values of that obtained with untreated BSA were deducted to get the values of net protein carbonyl formed. The results are given in table 1.

Example 3
Physico-Chemical Properties of the cs-Oxidant (a) Appearance: When crystallized from acetone solution, the oxidant appeared as small needle shaped faint yellow coloured crystals (FIG. 8). In the dry condition or in solution, the compound gradually turns brown in air under light.

(b) Odour: Pungent smell, similar to that of rancid butterfat.

(c) UV absorption: The oxidant has two absorption maxima in methanol solution, one at 293.4 nm and another at 223.0 nm (FIG. 9). In aqueous solution, the absorption maxima are at 288 nm and 221 nm. There was no absorption in the visible region of 400 nm to 700 nm indicating that the oxidant lacks chromophoric group.

Example 4
Chemical Properties of the cs-Oxidant (a) Solubility:

Highly soluble in methanol, ethanol, acetone, n-butanol, fairly soluble in water, sparingly soluble in methylene chloride, di-ethyl ether, chloroform and insoluble in benzene, petroleum ether.

(b) Effect of pH:

In acidic pH (4–5), the compound does not turn brown but looses its oxidizing potency. On keeping the solution at alkaline pH (pH 9), the compound gradually turns brown. At pH near 10 and above, there is instantaneous darkening with loss of both activity and aromaticity as evidenced by UV spectroscopy.

(c) Stability of the Solid Oxidant:

The half-life of the oxidant, when stored in the solid state at the room temperature under darkness, has been found to be 48 hours as determined by its ability to oxidize ascorbic acid (FIG. 10). The oxidation of ascorbic acid was measured by HPLC analysis. A standard curve of ascorbic acid, prepared using different concentrations of ascorbic acid, is shown in FIG. 11.

To determine the stability of the cs-oxidant, freshly prepared oxidant was distributed in five separate sample tubes. Each tube contained 5 µg of cs-oxidant. One tube was immediately examined (day0, FIG. 10) to determine its capacity to oxidize ascorbic acid. Other tubes were examined subsequently on day 1, 2, 3 and 5 respectively (FIG. 10). To each tube, 5 µg of ascorbate in 200 µl of 50-mM potassium phosphate buffer was added and incubated for 45 min at the room temperature. After that, 16 µl of the assay mixture was withdrawn at different time intervals and added to 24 µl of the mobile solvent to make the final volume to 40 µl. Twenty µl of this diluted solution, initially equivalent to 200 ng of ascorbic acid, was injected. A parallel control was kept without the oxidant to monitor the autoxidation of ascorbate. Ascorbic acid was detected at 254 nm. Under the conditions, retention time of ascorbic acid was 6.1 min. The minimum amount of ascorbate that could be determined by HPLC under the condition was 500 pg.

The conditions of HPLC analysis were

| | |
|---|---|
| Instrument: | Shimadzu 10A |
| Column: | Lichro CART 250-4 $NH_2$ column (Merck) |
| Mobile solvent: | Acetonitrile: 50 mM $KH_2PO_4$ (75:25) |
| Flow rate: | 1.5 ml/min |
| Pressure: | 132 $kgf/cm^2$ |
| Temperature: | 25° C. |

(d) Stability of the Oxidant in Solution

In contrast to the half-life of 48 hours when stored in the solid condition, the half-life of the oxidant was about 1 hour 30 min when stored in solution of 50 mM potassium phosphate buffer, pH 7.4 at 25° C. (FIG. 12).

The assay condition was same as described above under 'stability of the solid oxidant'.

(e) Reaction with Ferric Chloride Solution

To 200 µl methanol solution containing 500 µg of the cs-oxidant, 20 µl of aqueous solution of ferric chloride (1 mg) was added. An instant transient green colour appeared. This indicates that the oxidant contains phenolic —OH group.

(f) Reduction of Ferricytochrome c

The oxidant not only oxidizes proteins and ascorbic acid (as shown later), but also reduces ferricytochrome c quantitatively as measured by the formation of ferrocytochrome c with time (FIG. 13).

To 890 µl of 50-mM potassium phosphate buffer, pH 7.4, 100 µl of 1 mM ferricytochrome c solution was added to obtain a final concentration of 100 µM. To this was added a solution of 4.5 µg cs-oxidant in 10 µl of 50-mM potassium phosphate buffer, pH 7.4 and the absorbance was recorded at 550 nm at 30-second intervals. The results (FIG. 13) indicate that 1 nmole of the oxidant (taking M.W=110 as shown later) reduce 0.71 n mole of ferreicytochrome c, which approximates the molar ratio of 1:1. Or in other words, it appears that the oxidant contains one reducing group per molecule. Molar extinction coefficient of ferrocytochrome c at 550 nm was taken as $25 \times 10^3$ cm$^{-1}$. It was also observed that the reduction of ferricytochrome c by hydroquinone was approximately in the molar ratio of 1:0.71, indicating that the reducing component of the cs-oxidant is similar to that of hydroquinone.

(g) Oxidation of Ascorbic Acid

Oxidation of ascorbic acid by freshly prepared solution of the cs-oxidant was measured by HPLC analysis of ascorbic acid as described before under stability of the solid oxidant (item c under chemical properties of the cs-oxidant).

Ascorbate oxidation was measured using both limiting amount of ascorbate (28.41 nmoles) and excess of ascorbate (85.23 nmoles) with respect to a fixed amount of the oxidant (45.45 nmoles) in a final volume of 200 μl of 50 mM potassium buffer, pH 7.4. Aliquots were withdrawn at different time intervals as discussed in item c under chemical properties of the cs-oxidant and ascorbate was assayed by HPLC analysis. A similar result of ascorbate oxidation was obtained irrespective of using high amount (85.23 nmoles) or limiting amount (28.41 nmoles) of ascorbate.

After 45 min of incubation, the ratio of nmoles of ascorbate oxidized to nmoles of the cs-oxidant was 0.55 (Table 2). This ratio is actually 1:1, because oxidation of ascorbate is one electron transfer reaction and the product, ascorbate radical (AH.), is chemically inert and decays by disproportionation reaction as shown below.

$$2AH_2 + 2OX = 2AH. + 2OXH$$

$$2AH. = AH_2 + A$$

$$2AH_2 + 2OX = AH_2 + A + 2OXH$$

(AH$_2$=ascorbate, A=dehydroascorbate, OX=oxidant) [(Bielski, B. H. Jr. and Richter, H. W. (1975), Some properties of the ascorbate free radical. Ann. N.Y. Acad Sci, 258, pp. 231–237)]. The results obtained on ascorbate oxidation and ferricytochrome c reduction (item f above) indicate that the cs-oxidant contains one oxidizing group and one reducing group in the molecule in stoichiometric proportion.

Example 5

Quantitative Measurement of the cs-oxidant

The oxidant can be quantitatively measured by (a) UV spectroscopy (b) HPLC analysis and (c) reduction of ferricytochrome c.

(a) UV Absorption

5 μg of the oxidant was dissolved in 1 ml of HPLC grade methanol and UV absorption of the solution was recorded at 200–500 nm against methanol in a Hitachi double beam spectrophotometer (model U3020).

FIG. 9 shows that the oxidant has two absorption maxima (λ max).

| λ max | absorption |
|---|---|
| 293.4 nm | 0.3192 |
| 223.0 nm | 0.6994 |

The absorption at 293.4 nm was proportional to the concentration of the oxidant. The molar extinction coefficient of the oxidant based on its absorption maximum at 293.4 nm was calculated from FIG. 9 and found to be $\epsilon_{293.4} = 7018$ cm$^-$ (b) HPLC Analysis Different concentrations of the oxidant ranging from 10 ng to 100 ng in 20 μl of the mobile solvent were injected in the HPLC and the oxidant was detected at 294 nm. A standard curve was prepared (FIG. 14) based on the peak area (arbitrary) of the oxidant. The minimum amount of the oxidant that could be detected by the HPLC analysis under the condition was 500 pg.

The parameters used were:

| | |
|---|---|
| Instrument: | Shimadzu 10A |
| Column: | 25-cm silica column (LiChrospher ® Si 60, Merck) |
| Mobile solvent: | Methylene chloride: methanol (90:10, v/v) |
| Flow rate: | 0.5 ml/min |
| Pressure: | 29 Kgf/cm$^2$ |
| Temperature: | 25° C. |
| Retention time: | 8.808 min |

(c) Reduction of Ferricytochrome c

Different amounts of the cs-oxidant ranging from 1 μg to 5 μg were used to reduce ferricytochrome c according to the method described under item (f) under chemical properties of the oxidant. A standard curve was drawn based on the results obtained (FIG. 15).

Example 6

Determination of the Structure of the cs-Oxidant

The structure of the oxidant was determined by the following parameters: Elemental analysis, mass spectroscopy, melting point determination, UV spectroscopy, fluorescence spectroscopy, FTIR, H-NMR, C-NMR, ESR and XRF analysis.

(a) Elemental Analysis

Using 1 mg of the oxidant, elemental analysis was performed in PERKIN ELMER 2400 Series 11 CHNS/O Analyser.

Results

| Carbon % | Hydrogen % | Nitrogen % |
|---|---|---|
| 64.06 | 5.33 | 1.16 |

The ratio of C, H and O from this percentage analysis was:

| | |
|---|---|
| Carbon: | 5.34 |
| Hydrogen: | 5.33 |
| Oxygen (by difference): | 1.84 |

So the empirical formula is $C_6H_6O_2$ (b) Mass Spectroscopy

Molecular weight of the oxidant was determined by VG 7070 H mass spectrometer using EI technique at 70 eV. The observed molecular weight was 110 with two subsequent fragments of m/e 81 and 53 respectively (FIG. 16). Although the molecular weight of the compound appears to be that of hydroquinone ($C_6H_6O_2$), the compound is actually a strong oxidant. Comparative H-NMR spectroscopic studies (shown later) indicate that the oxidant has less amount of heteroatom-linked proton than that of hydroquinone and the g factor calculated from ESR spectroscopy (shown later) indicate that the compound is p-benzosemiquinone (MW 109). The observed molecular weight of 110 of the compound may be explained by the fact that the mass spectra was done with a sample stored for 7 days at the room temperature. It is possible that on storage in the solid state at the room temperature, p-benzosemiquinone is converted to its cationic form. It has been observed that on storage for 5–7 days in the solid state, the compound gives a UV absorption spectrum similar to that of hydroquinone (MW 110), accompanied by loss of oxidant activity (shown later).

(c) Melting Point Determination

The melting point of the cs-oxidant was found to be 162° C. Initially the oxidant appeared as a bunch of dark blackish rod like crystals under the microscope. With increase in temperature from about 140° C., the brightness at the edge of the crystals increased and there was separation of one crystal from another. The blackish shade from the edge of the crystals started disappearing and the distinctness and shine of the crystals increased as the temperature approached near the melting point. After just melting of most of the major portion of the crystals at 162° C., a few tiny rod like crystals appeared in the melted pool that subsequently melted at 172° C., which is known to be the melting point of hydroquinone. It is possible that at the high melting temperature, a portion of the oxidant was converted to hydroquinone. Under similar conditions, the melting point of hydroquinone was found to be 172° C. The characteristic change in the pattern of the crystals of the oxidant before melting as described above was less distinct in the case of hydroquinone.

Mixed Melting Point Studies

Equal amounts of hydroquinone and the cs-oxidant were dissolved in acetone and dried to get the mixed crystals. The melting point of the mixed crystals was found to be 165° C.

From the melting point experiment it is evident that the compound is not hydroquinone.

(c) UV Spectrophotometric Analysis

Five μg of the oxidant was dissolved in 1 ml methanol and the wave length scanning was monitored from 500 nm to 200 nm against methanol as the blank in a Hitachi double beam spectrophotometer, model U3020.

The absorption maxima as indicated in FIG. 9 are as follows:

| λ max | absorption |
|---|---|
| 293.4 nm | 0.3192 |
| 223.0 nm | 0.6994 |

Ratio of the absorption at λ max 223 nm:λ max 293.4 nm=2.19

The UV spectrophotometric analysis of hydroquinone under similar condition produced a ratio of 1.98 (FIG. 17), which was different from that of the oxidant. It is interesting to note that on storage at room temperature in the dark for upto eight days, the UV-spectra of the stored oxidant was more similar to that of hydroquinone giving a ratio of 1.99 (FIG. 18). This would indicate that on storage the cs-oxidant is converted slowly to hydroquinone.

On storage there was no indication of the formation of p-benzoquinone. When p-benzoquinone is mixed with hydroquinone in equimolar proportion, the absorption spectrum shows a shoulder near 242 nm (FIG. 19). Such shoulder is completely absent in the stored oxidant (FIG. 8).

(e) Fluorescence Spectroscopy

Using excitation wavelength at 294 nm, FIG. 20 shows that the fluorescent emission pattern of the oxidant is similar to that of hydroquinone under identical conditions (cf. FIG. 6*a*).

(f) FTIR Spectroscopy

FTIR spectroscopic analysis of the oxidant was carried out in the FTIR-8300 spectrophotometer, Shimadzu, Japan. With 1 mg of dry oxidant, a KBr pellet was prepared and used for FTIR spectroscopy FIG. 21 indicates peaks corresponding to O—H stretching at 3234.4 $cm^{-1}$
C—H stretching for aromatic ring at 3030.0 $cm^{-1}$
C—C— stretching at 1514.0 $cm^{-1}$
O—H bending at 1355.9 $cm^{-1}$
C—O stretching at 1193.9 $cm^{-1}$
C—H bending at 756.0 $cm^{-1}$ The FTIR spectrum of hydroquinone was carried out under similar conditions and it gave a comparable pattern of peaks (FIG. 22) with some subtle difference.

(g) NMR Spectroscopy

NMR spectroscopy was done using the Bruker 500 MHz spectrometer. Analysis and interpretation:

1H-NMR:

200-μg oxidant was dissolved in 500 μl $CD_3COCD_3$ and analyzed. The NMR profile shows one sharp peak at 6.56 ppm corresponding to the four aromatic protons of hydroquinone structure and another peak at 7.55 ppm corresponding to the heteroatom linked proton, the proton(s) linked to the oxygen atom in hydroquinone (FIG. 23). The H-NMR profile of hydroquinone in $CD_3COCD_3$ is given in (FIG. 24). There is no difference in the chemical shift of the two peaks between hydroquinone and the oxidant.

In deutereated acetone, the ratio of the aromatic protons to the heteroatom-linked protons for hydroquinone was found to be 1:0.4143. For the oxidant, this particular ratio was 1:0.2589. This shows that the oxidant contains less amount of heteroatom linked proton than that of hydroquinone. FIG. 25 shows that there is a distinct difference between the nature of the peaks of the oxidant and that of hydroquinone at 7.55 ppm.

When a pinch of sodium dithionite was added to the oxidant solution in $CD_3COCD_3$, the ratio of the aromatic protons to the heteroatom linked protons became 1:0.36. This indicates that the oxidant is reduced to hydroquinone by dithionite (FIG. 26).

C-NMR:

The C-NMR profile of the oxidant (FIG. 27) indicates that this is identical to that of hydroquinone (FIG. 28). In both the cases, with protons completely decoupled and using $CD_3COCD_3$ as the solvent, peaks have been obtained at 116.101 ppm and 150.695 ppm respectively. The peak at 150.695 ppm represents heteroatom (>C=O) linked carbon.

(h) XRF Analysis

All analyses, described so far, lead to the idea that the structure of the cs-oxidant is similar to that of hydroquinone except that it contains less amount of heteroatom linked proton. Moreover, in contrast to hydroquinone, the cs-oxidant is a strong oxidant. Using 1 mg BSA in 200-μl-incubation mixture containing 50 mM potassium phosphate buffer, pH 7.4, 10 μg of the oxidant produced 9 nmoles of carbonyl in 1 hour. Under similar conditions, 10 μg of hydroquinone produced negligible amount of protein carbonyl. Also in contrast to hydroquinone, the oxidant oxidizes ascorbate stoichiometrically. It would thus appear that the cs-oxidant might be either a transition metal complex of hydroquinone or a free radical, namely, p-benzosemiquinone containing an unpaired electron. For detecting the presence of metal, if any, the compound was subjected to X-ray fluorescence spectroscopy.

The oxidant was analyzed in the form of a pressed pellet after mixing with milled soil sample with boric acid backup.

The major and trace elements were determined using Philips PW 2404 wavelength dispersive x-ray fluorescence spectrometer (WDXRF) with a Rhodium x-ray tube. Operating conditions were 50 KV and 40 mA.

XRF analysis did not indicate the presence of any transition metal in the compound. Thus the strong oxidizing property of the compound was not due to the presence of any transition metal.

(i) ESR Analysis

Since the compound does not contain any transition metal as evidenced by XRF analysis, the other alternative remains that the oxidant is a free radical, most likely p-benzosemiquinone. To detect the presence of an unpaired electron, the oxidant was subjected to ESR spectroscopic analysis using two different approaches.

Approach #1. Since on storage, the activity of the cs-oxidant undergoes decay, ESR spectroscopy was studied with freshly prepared oxidant. Tar from 100 cigarettes was pooled and the oxidant purified on the same day and subjected to ESR spectroscopy.

The instrument used was JES-REIX ESR spectrometer (Tokyo, Japan).

The parameters used were:

| | |
|---|---|
| Field modulation width = | 0.4 mT |
| Temperature = | 25° C. |
| Power = | 2 mW |
| Scan field = | (335 ± 10) mT |
| Sweep time = | 8 min or 2.5 mT per min |
| Time constant = | 0.3 sec |
| Receiver gain = | 3.2 × 1000 |

The ESR profile (FIG. 29) shows the presence of a single symmetrical Lorentzian line. This is indicative of a single type of radical consisting of an unpaired electron delocalised over an aromatic framework. The spectroscopic splitting factor or the g-factor was calculated with reference to a standard solid DPPH (di-phenyl picryl hydrazyl) radical. The difference in positions of the exact centers (where the $1^{st}$ derivative signals crossed zero) of the cs-oxidant and the DPPH is 13 mm, corresponding to 1.8 G.

Since both spectra were recorded at the same fixed frequency, the frequency (ν) at which resonance occurs (hν=gBH) is the same for both spectra:

$h.\nu_{DPPH}=g_{DPPH}.B.H_{DPPH}$ and $h.\nu_{cs\text{-}oxidant}=g_{cs\text{-}oxidant}.B.H_{cs\text{-}oxidant}$ Since $\nu_{DPPH}$ and $\nu_{cs\text{-}oxidant}$ are the same $g_{DPPH}.B.H_{DPPH}=g_{cs\text{-}oxidant}.B.H_{cs\text{-}oxidant}$ B is a constant, therefore $g_{DPPH}.H_{DPPH}=g_{cs\text{-}oxidant}.H_{cs\text{-}oxidant}$ $H_{DPPH}$ is about 3353.15 G and therefore $H_{cs\text{-}oxidant}$ would be (3353.15 G−1.8 G)=3351.35 G.
Rearranging gives: $g_{cs\text{-}oxidant}$=2.0036×3353.15/3351.35= 2.00468

This g-value of the cs-oxidant is almost identical to the g-value of p-benzosemiquinone (2.004679±0.000006) reported before (Wertz, J. E. and Bolton, J. R. Electron spin resonance, theory and practical applications, McGraw-Hill Book Company, New York, 1972, p. 465).

The spin density of the cs-oxidant was calculated using standard picein as a reference and found to be $1.82\times10^{13}$ mg$^{-1}$ for 100 cigarettes or, the spin density=$1.82\times10^{11}$/cigarette Approach #2. Tar from 400 cigarettes, collected in batches each day, was pooled together during 7 days and stored at −72° C. Purification of the cs-oxidant from pooled tar was carried out during the next two days. ESR spectroscopy of the purified oxidant (8 mg) was carried out on the $10^{th}$ day.

FIG. 30 shows the ESR spectrum of the aged cs-oxidant collected from 400 cigarettes.

The spin density of the molecule was calculated using standard picein as before and found to be $1.0713\times10^{13}$ mg$^{-1}$ (From 400 cigarettes) or, $0.2678\times10^{11}$/cigarette It should be noted that the spin density of the aged cs-oxidant ($0.2678\times10^{11}$/cigarette), purified during 10 days as stated in approach #2, is only about 15% of the spin density ($1.82\times10^{11}$/cigarette) of the freshly prepared cs-oxidant (approach #1). This loss of paramagnetism was accompanied by about 85% loss of the oxidant activity of the aged cs-oxidant, as evidenced by the capacity to oxidize ascorbic acid. The result is corroborative of the fact that the paramagnetism accompanied by the oxidizing activity of the cs-oxidant decays on storage.

Molecular Structure of the cs-Oxidant

Based on the results obtained with HPLC analysis as well as chemical and spectroscopic studies, the molecular structure of the cs-oxidant can be derived as follows.

(i). The cs-oxidant contains an unpaired electron and its g-value is identical to that of p-benzosemiquinone.

(ii). The structure is similar to that of hydroquinone with the exception that its M.P. is low (162° C.) & it contains less amount of heteroatom linked proton than that of hydroquinone. On reduction with $Na_2S_2O_4$, the oxidant is converted to hydroquinone.

(iii) In contrast to hydroquinone, the cs-oxidant is a strong oxidizing agent. It oxidizes protein as well as ascorbic acid.

(iv) The oxidant also contains a reducing group as evidenced by the reduction of ferricytochrome c.

(v) The reduction of ferricytochrome c and oxidation of ascorbic acid are stoichiometric; that is the molecule contains one reducing group and one oxidizing group in stoichiometric proportion. The phenolic OH attributed the reducing property and the oxygen with unpaired electron attributes the oxidizing property. It would thus appear that the molecular structure of the cs-oxidant is p-benzosemiquinone, as shown below.

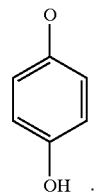

p-Benzosemiquinone may exist in different mesomeric forms, namely, anionic, neutral or cationic forms, as depicted in FIG. 1, indicating delocalization of an unpaired electron over an aromatic frame work containing heteroatoms. This is why p-benzosemiquinone is a relatively stable free radical, which could be isolated from cigarette smoke solution in the solid crystalline state. Nevertheless, on storage the isolated pure oxidant loses the paramagnetism accompanied by loss of the oxidant activity as shown above under ESR studies. The half-life of the oxidant is 48 hours when stored at the room temparature in the solid state under darkness and about 1.5 hours when stored in solution of 50 mM potassium phosphate buffer, pH 7.4.

Example 7
The Purified cs-Oxidant Alone Quantitatively Accounts for the Protein Oxidation Produced by the Whole Cigarette Smoke Solution Using BSA oxidation as a model system, the aforesaid statement has been substantiated by the following observations.

(i) BSA oxidation produced by the whole cs solution as evidenced by cabbonyl formation, is retained in the purified cs oxidant (stable one). The components of the whole cs solution discarded in the various steps of isolation and purification of the oxidant such as solvent extraction, TLC and HPLC did not produce BSA oxidation. For example, at the stage of solvent extraction, BSA oxidation was practically nil by the methylene chloride extract (Step 2, under Isolation and purification)

(ii) TLC of the lyophilized material (Step 4, under Isolation and purification) produced six bands including the band of the cs-oxidant at $R_f$=0.26 as shown in FIG. 2. Extracts of all the bands were collected separately as described before and used for BSA oxidation. BSA oxidation was produced only by the extract of the band corresponding to $R_f$=0.26 containing the cs-oxidant. Extracts of all other bands having Rf=0.12, 0.14, 0.16, 0.30, 0.80 as well as that from the base line, when used separately or conjointly, did not produced BSA oxidation.

(iii) During HPLC of the butanol extract at the penultimate stage of purification procedure (Step 6, under Isolation and purification), only the effluent from the major peak (retention time 8.808 min, FIG. 3b) corresponding to the cs-oxidant produced BSA oxidation. Other minor peaks having retention times ranging from 4.55 min to 7.25 min did not produce BSA oxidation.

(iv) HPLC analysis of the whole cs solution using the silica column indicated the presence of several peaks having retention times ranging from 5.717 min to 17.782 min including a major peak of the cs oxidant having retention time 8.813 min (FIG. 3I). When instead of the whole cs solution, aqueous extract of cs was used, the oxidant eluted out at a retention time of 8.808 min (FIG. 32), which is identical to the peak of the cs-oxidant having retention time of 8.808 min as revealed by HPLC analysis of the pure cs-oxidant (FIG. 4). Only the effluent from the peak corresponding to the cs-oxidant (retention time 8.813 min) produced BSA oxidation. Effluents from all other peaks separately or conjointly did not oxidize BSA.

(v) HPLC analysis of the whole cs solution was also carried out using ODS column. The parameters used were:

Column: Shim-pack CLC-ODS (M)
Mobile solvent: water:methanol (95:5)
Flow rate: 0.8 ml/min
Pressure: 147 kgf/cm$^2$
Temperature: 25° C.
Absorbance: 288 nm ($\lambda$ max of the cs-oxidant in water)

HPLC analysis of the whole cs solution using the ODS column produced about 13 peaks including a major peak at 13.467 min (FIG. 33), which is the peak of the cs-oxidant as evidenced by the HPLC analysis of the pure cs-oxidant (retention time 13.46 min, FIG. 34). Under this condition also, as observed using the silica column as stated before, only the effluent from the peak corresponding to the cs-oxidant (retention time 13.46 min) produced BSA oxidation. Effluents from the other peaks separately or conjointly did not oxidize BSA.

It should be mentioned that although the resolution obtained using the ODS column was better than that of the silica column, the ODS column could not be routinely used for analyzing cigarette smoke solution or the cs-oxidant. After a few run with whole cs solution, aqueous extract of cs or the cs-oxidant, the ODS column underwent degeneration as evidenced by increased backpressure and loss of capacity of resolution.

The aforesaid results indicate that only the cs-oxidant is responsible for the oxidation of BSA. No other component of the whole cs solution can oxidize BSA. This is further confirmed by the results presented in Table 3. The table shows that when the whole cs solution is used, a peak area of 17030×10$^3$ corresponding to the cs-oxidant (retention time, 8.813 min) produces 7.53 nmoles of carbonyl, which is equivalent to 4.42×10$^{-7}$ nmole of carbonyl per unit area. The table (Table 3) further shows that when instead of the whole cs solution, the HPLC-purified cs-oxidant is used, a peak area of 19010×10$^{13}$ having retention time 8.808 min produces 9.56 nmoles of carbonyl, which is equivalent to 5.03×10$^{-7}$ nmole of carbonyl per unit area. The results indicate that the oxidation of BSA produced by the whole cs solution is almost quantitatively reproduced separately by the pure oxidant alone when the latter is used in amount corresponding to that present in the whole cs solution.

The cs-oxidant not only quantitatively accounts for the oxidative damage of proteins caused by the whole cs solution, but also it is a major hazardous component of the cigarette smoke as evidenced by its content. From HPLC analysis (p. 8, under recovery of the cs-oxidant), it is observed that the cs-oxidant present in one ml of the whole cs solution (equivalent to one cigarette) gives an arbitrary area of 3.4×10$^8$. From the standard HPLC curve, 100 ng of pure cs-oxidant gives an area of 190000. So the content of the cs-oxidant in the whole cs solution from one cigarette is about 190±10 µg. Comparable yields were obtained from 12 different brands of commercial cigarette with or without standard filters. It should be mentioned that the cs-oxidant is not present in nonsmoking tobacco but formed during burning of the cigarette.

That the purified cs-oxidant quantitatively accounts for the oxidative damage of proteins produced by the whole cs solution is further evidenced by SDS-PAGE of the guinea pig lung microsomal proteins treated with whole cs solution as well as the cs-oxidant (FIG. 35a). The figure shows that compared to untreated microsomes (lane 1), substantial damage is produced by 50 µl cs solution (lane 2) and 100 µl cs solution (lane 3) respectively. When the cs solution is replaced by pure cs-oxidant in amounts present in the cs solution, the damage is even more as depicted in lane 4 (10 µl g cs-oxidant) and lane 5 (20 µg cs-oxidant). FIG. 35b shows densitometric scanning of the protein bands of different lanes (lane 1–5), indicating graphical representation of the comparative extent of damage produced by cs solution and the cs-oxidant in amounts present in the cs solution.

Example 8
cs-Oxidant Induced Oxidative Damage of DNA

It has been reported that cigarette smoke solution produces DNA damage as evidenced by single strand break and formation of 8-hydroxyguanosine. It is also known that DNA damage is implicated with mutation and cancer. About 80% of the lung cancer in the world is caused by cigarette smoke. Now the applicants produce data to indicate that cigarette smoke-induced oxidative damage of DNA is caused by the cs-oxidant. Two mg of plasmid DNA was incubated with 15 µg of cs-oxidant in 50 mM potassium phosphate buffer, pH 7.4 at 37° C. for one hour in a final volume of 200 µl. A control incubation system was kept without cs-oxidant. After incubation, the DNA was precipitated with 500 µl of ethanol, centrifuged, washed free of salt with 70% ethanol, lyophilized, stored at −70° C. and subsequently analyzed for oxidative damage. The DNA damage was measured by the production of 8-hydroxyguanosine and 5-hydroxy-6-methyl hydantoin using GC-mass. The results show that cs-oxidant induces the formation of 24 nmoles of 8-hydroxyguanosine and 121 nmoles of 5-hydroxy-6-methyl hydantoin per $10^6$ DNA bases.

Example 9
Prevention of cs-Oxidant Induced Protein Oxidation by Different Chemical Compounds/Agents A number of chemical compounds/agents have been identified those prevent oxidation of BSA in vitro to the extent of 35 to 97%. The chemical compounds/agents include, besides ascorbic acid, tartaric acid, citric acid, oxalic cid, glutathione, tea extract and individual components of tea (Table 4).

TABLE 1

Estimation of oxidative potency at different stages of purification of the cs-oxidant

| Stage | Purification step | Oxidation of BSA (nmoles of carbonyl/mg of BSA) | Amount of material used for BSA oxidation | Specific activity** (nmoles of carbonyl/mg of dry weight) |
|---|---|---|---|---|
| 1. Whole cs-solution or tar solution | 1 | 7.53 ± 0.34 | 0.6 mg* | 12.55 |
| 2. Aqueous extract of cs | 2 | 8.16 ± 0.24 | 0.4 mg* | 20.4 |
| 3. Butanol Fraction | 3 | 7.80 ± 0.20 | 0.11 mg* | 70.90 |
| 4. Acetone extract after TLC | 4 | 9.23 ± 0.14 | 0.015 mg | 615.3 |
| 5. Pure exident after HPLC | 6 | 9.56 ± 0.14 | 0.010 mg | 956.0 |

*Actual weight after deducting the dry weight of the salt present in 50 µl of potassium phosphate buffer solution.
**Mean values are given, S.D < 5% (n = 10)

TABLE 2

Oxidation of ascorbic acid by the cs-oxidant as measured by HPLC analysis

| Time of incubation (min) | Arbitrary area in HPLC | Amount of ascorbate estimated (nmoles) | Gross oxidation (nmoles) | Auto oxidation (nmoles) | Net ascorbate oxidation (nmoles) |
|---|---|---|---|---|---|
| 0 | 188170 | 28.4 | — | 0 | — |
| 0.5 | 175672 | 26.5 | 1.9 | 0 | 1.9 |
| 5 | 145024 | 21.9 | 6.5 | 0 | 6.5 |
| 15 | 102636 | 15.5 | 12.9 | 0.9 | 12 |
| 30 | 45885 | 6.9 | 21.5 | 1.8 | 19.7 |
| 45 | 3628 | 0.5 | 27.9 | 2.7 | 25.2 |

TABLE 3

BSA oxidation by fractions of CS-solution at different stages of purification

| Fractions | Amount used | Retention time (min) of the cs-oxidant peak | Arbitrary area of the peak | nmoles of carbonyl produced/mg BSA | nmoles of carbonyl per unit area of the oxidant × $10^7$ |
|---|---|---|---|---|---|
| 1. Whole as solution* | 50 µl (600 µg) | 8.813 | 17030 × $10^3$ | 7.53 ± 0.34 | 4.42 ± 0.20 |
| 2. Aqueous extract of cs | 50 µl (400 µg) | 8.808 | 14785 × $10^3$ | 8.16 ± 0.24 | 5.52 ± 0.16 |
| 3. cs-oxidant purified by TLC | 10 µl (15 µg) | 8.808 | 19063 × $10^3$ | 9.23 ± 0.14 | 4.84 ± 0.07 |
| 4. cs-oxidant purified by HPLC | 10 µl (10 µg) | 8.808 | 19010 × $10^3$ | 9.56 ± 0.14 | 5.03 ± 0.07 |

*Similar results were obtained when whole cs solution was replaced by equal amount of tar solution.

TABLE 4

Protection of cs-oxidant-induced albumin oxidation by different chemical agents.

| Ser. No. | Agents used | Concentration/amount | % Protection |
|---|---|---|---|
| 1 | Ascorbic acid | 100 µM | 76 |
| 2 | Sodium dithionite | 2 mM | 97 |
| 3 | Tartaric acid | 1 mM | 75 |
|   | Tartaric acid | 500 µM | 67 |
| 4 | Citric acid | 1 mM | 75 |
|   | Citric acid | 500 µM | 67 |
| 5 | Oxalic acid | 500 µM | 53 |
| 6 | Succinic acid | 1 mM | 60 |
| 7 | Histidine | 1 mM | 67 |
| 8 | Black tea extract | 2.5 mg | 50 |
| 9 | Catechin | 750 µg | 54 |
| 10 | Epigallocatechin | 140 µg | 95 |
| 11 | Epicatechin | 50 µg | 50 |
| 12 | Green tea extract | 2.5 mg | 50 |
| 13 | Lysine | 1 mM | 35 |
| 14 | Thiourea | 10 mM | 52 |
| 15 | Glutathione | 1 mM | 37 |

The incubation system and carbonyl estimation are described in the text.

TABLE 5

Inactivation of the major harmful cs-oxidant and nicotine delivery in cigarette smoke using activated charcoal filter

| Size and weight of active charcoal used | Fortification with nicotine (mg) | Length of the cigarette tobacco (mm) | Length of the◆ conventional filter (mm) | Length of the* charcoal filter (mm) | % inhibition of BSA oxidation | % of nicotine delivered in the smoke |
|---|---|---|---|---|---|---|
| None | — | 63 mm | 11 | None | — | 100** |
| BS 44, 0.6 gm# | None | 63 mm | 8 + 3 | 26 | 68 | 46 |
| BS 44, 0.6 gm# | 3 | 63 mm | 8 + 3 | 26 | 68 | 74 |
| BS 44, 0.6 gm# | 4 | 63 mm | 8 + 3 | 26 | 68 | 98 |
| BS 44 + BS 52≠ 0.6 gm  0.2 gm | None | 63 mm | 7 + 3 + 3 | 26 + 9 • | 89 | 30 |
| BS 44 + BS 52≠ 0.6 gm  0.2 gm | 3 | 63 mm | 7 + 3 + 3 | 26 + 9 | 89 | 65 |
| BS 44 + BS 52≠ 0.6 gm  0.2 gm | 4 | 63 mm | 7 + 3 + 3 | 26 + 9 | 89 | 90 |

*Internal diameter of the charcoal filter was 8 mm.
**The percentage was calculated taking nicotine delivered (940 μg ± 40 S.D; n = 6) from cigarette with conventional filter as 100
BS 44 indicates BS 25 (−) to BS 44 (+), particle size of 350–700 μm
≠ BS 52 indicates BS 44 (−) to BS 52 (+), particle size of 250–350 μm
• 26 mm BS 44 + 9 mm BS 52
◆The lengths of the conventional filters have been depicted in FIGS. 36 and 37.

REFERENCES

1. Bartecchi, C. E.; Mackenzie, T. D. and Schier, R. W. The human costs of tobacco use. N. Engl. J. Med. 330:907–912; 1994.
2. Frank, E. Benefits of stopping smoking. West J. Med. 159:83–87; 1993
3. U.S. Surgen General's Report. Department of Health, Education and Welfare; Deparment of Health and Human Services, USA; 1985
4. Shah, P. K.; Helfant, R. H. Smoking and coronary artery disease. Chest 94:449–452; 1988
5. Sherman, C. B. Health effect of cigarette smoking. Clin. Chest Med. 12:643; 1991, J. N.; Green, C. R.; Best, F. W. and Newell, M. P. Smoke composition: an extensive investigation of the water-soluble portion of cigarette smoke. J. Agric. Food Chem. 25:310–320; 1977
6. Cross, C. E. Moderator. Oxygen radicals and human disease. Ann. Intern. Med. 107:526–545; 1987
7. Panda, K.; Chattopadhyay, R.; Ghosh, M. K.; Chattopadhyay, D. J.; and Chatterjee, I. B. Vitamin C prevents cigarette smoke-induced oxidative damage of proteins and increased proteolysis. Free Radic. Biol. Med. 27:1064–1079; 1999
8. Eiserich, J. P.; Vossen, V.; O'Neill, C. A.; Halliwel, B.; Cross, C. E.; and Van der Vliet. A molecular mechanism of damage by excess nitrogen oxides: nitration of tyrosine by gas phase cigarette smoke. FEBS Lett. 353:53–56; 1994
9. Panda, K.; Chattopadhyay, R.; Chattopadhyay, D. J.; and Chatterjee, I. B. Vitamin C prevents cigarette smoke-induced oxidative damage in vivo. Free Radic. Biol. Med. 29,115–124, 2000
10. SchumacherNakayama, T.; Kaneko, M,; Kodama, M. and Nagata, C. Cigarette smoke induces DNA single strand breaks in human cells. Nature 314:462–464; 1985
11. Nakayama, T.; Kaneko, M,; Kodama, M. and Nagata, C. Cigarette smoke induces DNA single strand breaks in human cells. Nature 314:462–464; 1985
12. Borish, E. T.; Cosgrove, J. P.; Chirch, D.F.; Deutesch, W. A. and Pryor, W. A. Cigarette tar causes single-strand breaks in DNA. Biochem. Biophys. Res. Commun. 133:780–786; 1985
13. Denissoenko, M. F.; Pao, A.; Targ, M -S. and Pfeifer, G. P. Preferential formation of benzo [a] pyrene adducts at lung cancer mutational hotspots in P53. Science, 274:430–432; 1996
14. Fischer, S.; Spiegelhalder, B. and Preussmann, R. Tobacco specific nitrosamines in European and USA cigarettes. Arch Geschwulstforsch, 60:169–177; 1990
15. Church, D. F. and Pryor, W. A. Free radical chemistry of cigarette smoke and its toxicological implications. Environ. Health Perspect. 64:111–126; 1985
16. Pryor, W. A., Hales, B. J., Premovic, P. I. and Church, D. F. The radical in cigarette tar: Their nature and suggested physiological implication. Science 220:425–427, 1983.
17. Glantz, S. A.; Slade, J.; Bero, L. A.; Hanauer, P. and Barnes, D. E. The cigarette papers. University of California Press, Berkely, USA, 1996.
18. Nagata, C.; Kodama, M. and Ioki, Y. In Polycyclic Hydrocarbons and Cancer, Gelboin, H. V. and P.O.P. Ts'o, Eds. (Academic Press, New York), 1:247; 1978
19. Wertz, J. E. and Bolton, J. R. Electron spin resonance, elementary theory and practical applications. McGrow-Hill Book company, New York, 1972, p-213.

What is claimed is:

1. A process for the isolation of p-benzosemiquinone of formula 1

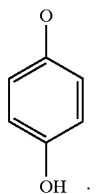

(Formula I)

a major harmful oxidant from cigarette smoke responsible for the oxidative damage of proteins and DNA, the said process comprising the steps of
 (a) collecting tar or cs (cigarette smoke) solution from lighted conventional filtered tipped cigarettes,
 (b) collecting tar by lighting conventional filter-tipped cigarettes having a tar content of 20–30 mg per cigarette in a glass flask dipped in a mixture of ice and salt and allowing the tar to condense and settle at the bottom of the flask, (c) keeping the above said flask at room temperature and extracting the said tar with 30–60 mM potassium phosphate buffer at a pH ranging between 7.4 to 7.8, filtering the above solution through 0.45 μm Millipore filter and adjusting the pH of the filtrate ranging between 7.4 to 7.6 by adding NaOH solution to obtain the desired tar solution, (d) extracting the above said tar solution thrice with equal volume of methylene chloride, discarding the lower methylene chloride layer and collecting the upper yellow coloured aqueous layer termed as aqueous extract of cigarette smoke, (e) extracting the above said aqueous extract of cigarette smoke twice with equal volume of water saturated n-butanol, lyophilizing the pooled yellow butanol extract in a lyophilizer at a temperature ranging between −50° C. to −60° C. under vacuum followed by extraction of the lyophilized material twice with HPLC grade acetone and drying the acetone solution under vacuum and dissolving the said acetone extract with HPLC grade methanol, (f) subjecting the above said methanol solution to band TLC using non-fluorescent silica plates, developing the said silica plates using a mixture of toluene and ethyl acetate in a ratio of 80:20, taking out the said plate and drying it at about 25–30° C. using a drier, cutting small strips containing the developed material from both sides of the plates and keeping them in an iodine chamber for the location of the band corresponding to Rf 0.26, scraping the band and extracting the band material with HPLC grade acetone followed by collection of the acetone layer and drying it under vacuum, (g) dissolving the above said acetone extract which appeared as pale yellow needles by adding equal volume of milli Q water, extracting the resultant aqueous solution with equal volume of HPLC grade water saturated n-butanol followed by drying upper n-butanol layer in small glass tubes under vacuum to obtain the major cigarette smoke (cs) oxidant with a purity of 98–99% and yield of about 18–22 μg per cigarette, (h) purifying the above said cs oxidant as obtained in step (g) by dissolving it in a mobile solvent comprising a mixture of methylene chloride and methanol in a ratio of 90:10 (v/v) and injecting it in a HPLC instrument with a normal phase 25 cm silica column using a uv detector at 294 nm at a flow rate of 0.5 ml/min, at a temperature of about 25° C. and at a pressure of about 29 kgf/cm$^2$ followed by collecting the effluent which appears as a single peak at a retention time of 8.808 min with a purity of 100% and yield of 8.4% of the total cs oxidant present in the parent tar solution.

2. A process as claimed in claim 1, wherein said isolated pure cigarette smoke (cs) oxidant has the following properties:

(a) when crystallized from acetone solution appears as small needle shaped faint yellow coloured crystals having pungent smell, similar to that of rancid butterfat, (b) UV absorption maxima in methanol solution are at 293.4 nm and 223.0 nm and in aqueous solution are in 288 nm and 221 mm, respectively, (c) on excitation at 293 nm in methanol solution the observed emission maxima are at 329.6 nm and 651.4 nm and on excitation at 224 nm, the observed emission maxima are at 329.6 nm and 652.6 nm, respectively, (d) when excitation scanning is monitored keeping the emission at 330 nm, the observed excitation maxima are at 228.2 nm and 293.8 nm and when the emission is kept at 651 nm and excitation scanning is monitored, the observed excitation maxima are at 229.2 nm and 294.8 nm, respectively, (e) highly soluble in methanol, ethanol, acetone, n-butanol, fairly soluble in water, sparingly soluble in methylene chloride, di-ethyl ether, chloroform and insoluble in benzene and petroleum ether, (f) the compound looses its oxidizing potency in acidic pH ranging between 4 to 5 and on keeping the solution at alkaline pH ranging between 9 to 10, the compound gradually turns brown, at pH 10 and above there is instantaneous darkening with loss of both activity and aromaticity as evidenced by UV spectroscopy, (g) the half-life of the oxidant, when stored in the solid state at a temperature ranging between 25° C. to 30° C. under darkness is about 48 hours as determined by its oxidative potency, but in solution of 50 mM potassium phosphate buffer, pH 7.4 at 25° C. to 30° C. the half life is about 1 hour 30 min, (h) reduces ferricytochrome c and ferric chloride, (i) oxidizes ascorbic acid, proteins and DNA, and (j) the melting point is 162° C.

3. A process for the quantitative determination of p-benzosemiquinone of formula 1, a major harmful oxidant isolated from cigarette smoke responsible for the oxidative damage of proteins and DNA, the said process comprising the steps of (a) collecting tar or cs (cigarette smoke) solution from lighted conventional filtered tipped cigarettes, (b) collecting tar by lighting conventional filter-tipped cigarettes having a tar content of 20–30 mg per cigarette in a glass flask dipped in a mixture of ice and salt and allowing the tar to condense and settle at the bottom of the flask, (c) keeping the above said flask at room temperature and extracting the said tar with 30–60 mM potassium phosphate buffer at a pH ranging between 7.4 to 7.8, filtering the above solution through 0.45 μm Millipore filter and adjusting the pH of the filtrate ranging between 7.4 to 7.6 by adding NaOH solution to obtain the desired tar solution, (d) extracting the above said tar solution thrice with equal volume of methylene chloride, discarding the lower methylene chloride layer and collecting the upper yellow coloured aqueous layer termed as aqueous extract of cigarette smoke, (e) extracting the above said aqueous extract of cigarette smoke twice with equal volume of water saturated n-butanol, lyophilizing the pooled yellow butanol extract in a lyophilizer at a temperature ranging between −50° C. to −60° C. under vacuum followed by extraction of the lyophilized material twice with HPLC grade acetone and drying the acetone solution under vacuum and dissolving the said acetone extract with HPLC grade methanol, (f) subjecting the above said methanol solution to band TLC using non-fluorescent silica plates, developing the said silica plates using a mixture of toluene and ethyl acetate in a ratio of 80:20, taking out the said plate and drying it at about 25–30° C. using a drier followed by cutting small strips containing the developed material from both sides of the plates and keeping them in an iodine chamber for the location of the band corresponding to Rf 0.26, scraping the band and extracting the band material with HPLC grade acetone followed by collection of the acetone layer and drying it under vacuum, (g) dissolving the above said acetone extract which appeared as pale yellow needles by adding equal volume of milli Q water, extracting the resultant aqueous solution with equal volume of HPLC grade water saturated n-butanol followed by drying upper n-butanol layer in small glass tubes under vacuum to obtain the major cigarette smoke (cs) oxidant with a purity of 98–99% and yield of about 18–22 μg per cigarette, and (h) purifying the above said cs oxidant as obtained in step (g) by dissolving it in a mobile solvent comprising a mixture of methylene chloride and methanol in a ratio of 90:10 (v/v) and injecting it in a HPLC instrument with a normal phase 25 cm silica column using a uv detector at 294 nm at a flow rate of 0.5 ml/min, at a temperature of about 25° C. and at a pressure of about 29 kgf/cm$^2$ followed by collecting the effluent which appears as a single peak at a retention time of 8.808 min with a purity of 100% and yield of 8.4% of the total cs oxidant present in the parent tar solution.

4. A process as claimed in claim 3, wherein p-benzosemiquinone present in cs solution is quantitatively assayed by HPLC with a UV detector using a 25 cm reverse phase ODS column and using a mixture of water and methanol (95:5 v/v) as a mobile phase, at a wave length of 288 nm, flow rate of 0.8 ml/min, at a temperature of about 25° C. and at a pressure of about 147 Kgf/cm2 and having a retention time of 13.46 min.

5. A process as claimed in claim 1, wherein p-benzosemiquinone present in cs solution is quantitatively assayed by HPLC with a UV detector using a 25 cm reverse phase ODS column and using a mixture of water and methanol (95:5 v/v) as a mobile phase, at a wave length of 288 nm, flow rate of 0.8 ml/min, at a temperature of about 25° C. and at a pressure of about 147 Kgf/cm2 and having a retention time of 13.46 min.

6. A process as claimed in claim 1, wherein the said p-benzosemiquinone is responsible for the major cause of oxidative damage of proteins isolated from the whole cs solution.

7. A process as claimed in claim 1, wherein p-benzosemiquinone, the cs oxidant is responsible for the oxidative damage of DNA.

8. A process as claimed in claim 1, wherein the damage of proteins caused by p-benzosemiquinone present in cs solution is quantitatively determined by measuring protein carbonyl formation by reacting the protein with p-benzosemiquinone obtained from the cs solution, followed by reaction with 2,4 dinitrophenyl hydrazine (DNPH) and finally measuring the absorbance at a wave length of 390 nm.

9. A process as claimed in claim 1, wherein the damage of proteins caused by p-benzosemiquinone present in cs solution is quantitatively determined by measuring oxidative degradation of guinea pig tissue microsomal proteins by reacting the said protein with p-benzosemiquinone present in cs solution followed by SDS-PAGE and densitometric scanning.

10. A process as claimed in claim 9, wherein the protein used for the assay of oxidative damages of protein is selected from the group consisting of BSA and guinea pig lung microsomal proteins.

11. A process as claimed in claim 9, wherein the BSA oxidation produced by the whole cs solution is effected by the p-benzosemiquinone present in the cs solution.

12. A process as claimed in claim 11, wherein the BSA oxidation produced by the cs oxidant as evidenced by nmoles of carbonyl formed per mg BSA is 9.56±0.14 in comparison to 7.53±0.34 produced by the whole cs solution.

13. A process as claimed in claim 11, wherein the BSA oxidation produced by the cs oxidant as evidenced by nmoles of carbonyl formed per mg BSA is 9.56±0.14 in comparison to 8.16±0.24 produces by the aqueous extract of cigarette smoke.

14. A process as claimed in claim 11, wherein the BSA oxidation produced by the cs oxidant as evidenced by nmoles of carbonyl formed per mg BSA is 9.56±0.14 in comparison to 9.23±0.14 produces by the TLC purified aqueous extract of cigarette smoke.

15. A process as claimed in claim 10, wherein the oxidative degradation of guinea pig tissue microsomal proteins produced by the p-benzosemiquinone solution as evidenced by SDS-PAGE is comparable to that produced by the whole cs solution.

16. A process as claimed in claim 1, wherein the said method is used for quantitative determination of cs oxidant p-benzosemiquinone in cigarettes based on the tar content of the particular commercial brand of the cigarette.

17. A process as claimed in claim 1, wherein the said method is used for quantitative determination of cs oxidant p-benzosemiquinone in cigarettes based on toxicity level of the particular commercial brand of the cigarette.

18. A process as claimed in claim 1, wherein the amount p-benzosemiquinone isolated from smoke of different commercial brands of burning cigarettes is used to determine the toxicity index of a particular brand of cigarette based on the quantity of p-benzosemiquinone present.

* * * * *